(12) United States Patent
Huang et al.

(10) Patent No.: US 8,163,480 B2
(45) Date of Patent: Apr. 24, 2012

(54) NUCLEIC ACID SIZE DETECTION METHOD

(75) Inventors: Donghui Huang, San Ramon, CA (US); Charles M. Strom, San Clemente, CA (US); Steven J. Potts, Flagstaff, AZ (US); Jenny Ellen Rooke, Seattle, WA (US)

(73) Assignees: Quest Diagnostics Investments Incorporated, Wilmington, DE (US); US Genomics, Inc., Woburn, MA (US)

( * ) Notice: Subject to any disclaimer, the term of this patent is extended or adjusted under 35 U.S.C. 154(b) by 366 days.

(21) Appl. No.: 11/544,293

(22) Filed: Oct. 5, 2006

(65) Prior Publication Data

US 2008/0124709 A1 May 29, 2008

(51) Int. Cl.
| | |
|---|---|
| C12Q 1/68 | (2006.01) |
| C12P 19/34 | (2006.01) |
| C07H 21/02 | (2006.01) |
| C07H 21/04 | (2006.01) |

(52) U.S. Cl. ....... 435/6.1; 435/91.2; 536/23.1; 536/24.3
(58) Field of Classification Search .................... None
See application file for complete search history.

(56) References Cited

U.S. PATENT DOCUMENTS

| | | | |
|---|---|---|---|
| 5,135,717 | A | 8/1992 | Renzoni et al. |
| 5,175,082 | A | 12/1992 | Jeffreys |
| 5,206,137 | A | 4/1993 | Ip et al. |
| 5,364,759 | A | 11/1994 | Caskey et al. |
| 5,580,990 | A | 12/1996 | Van den Berg et al. |
| 5,652,099 | A | 7/1997 | Conrad |
| 5,674,686 | A | 10/1997 | Schumm et al. |
| 5,714,327 | A | 2/1998 | Houthoff et al. |
| 5,985,566 | A | 11/1999 | Houthoff et al. |
| 6,013,444 | A | 1/2000 | Dau et al. |
| 6,074,831 | A | 6/2000 | Yakhini et al. |
| 6,268,132 | B1 | 7/2001 | Conrad |
| 6,767,703 | B2 | 7/2004 | Schumm et al. |
| 6,960,437 | B2 | 11/2005 | Enzelberger et al. |
| 2008/0113355 | A1 | 5/2008 | Hagerman et al. |

FOREIGN PATENT DOCUMENTS

| | | |
|---|---|---|
| EP | 0539466 | 11/1996 |
| WO | WO-94/28175 | 12/1994 |

OTHER PUBLICATIONS

Annemieke et al. (1991) Cell vol. 65, 906-914.*
Chen et al. (2003) Human Molecular genetics vol. 12 No. 23 pp. 3067-3074.*
New England Biolabs 1993/94 Catalog p. 13.*
Dobkin, C. et al., Am. J. Med. Genet., vol. 83, pp. 338-341 (1999).*
Larsen, L. A. et al., Hum. genet., vol. 100, pp. 564-568 (1997).*
Marino, M. A. et al., Electrophoresis, vol. 19, pp. 108-118 (1998).*
Muller, O. et al., Anal. Chem., vol. 67, pp. 2974-2980 (1995).*
Berka, J. et al., Electrophoresis, vol. 24, pp. 639-647 (2003).*
Oostra, B. A. et al., J. Med. Genet., vol. 30, pp. 410-413 (1993).*
Naidoo, R. et al., Pathology Oncol. res., vol. 4, pp. 310-315 (1998).*
Campuzano et al., Friedreich's Ataxia: Autosomal Recessive Disease Caused by an Intronic GAA Triplet Repeat Expansion, Science, 271, 1423-1427 (1996).
Chen et al., The $(CGG)_n$ repeat element within the 5' untranslated region of the FMR1 message provides both positive and negative cis effects on in vivo translation of a downstream reporter, Hum. Mol. Genetics 12(23):3067-74, (2003).
Fu et al., An Unstable Triplet Repeat in a Gene Related to Myotonic Muscular Dystrophy, Science, 255, 1256-1258 (1992).
Gebinoga, M. & Oehlenschlager, F., Comparison of self-sustained sequence-replication reaction systems, European Journal of Biochemistry, 235:256-261, (1996).
Hafner et al., Isothermal Ampllification and Multimerization of DNA by BST DNA Polymerase, Biotechniques, 4:852-6, 858, 860 (2001).
Heim et al., Highly sensitive detection of gene expression of an intronless gene: amplification of MRNA, but notgenomic DNA by nucleic acid sequence based amplification (NASBA), Nucleic Acids Res., 9:2250-2251 (1998).
Henegariu, Custom fluorescent-nucleotide synthesis as an alternative method for nucleic aci labeling, Nat. Biotechnol. 18:345-348, (2000).
Huntington's Disease Collaborative Research Group, A Novel Gene Containing a Trinucleotide Repeat That is Expanded and Unstable on Huntington's Disease Chromosomes, Cell, 72:971-983 (1993).
Jameson, D.M. and Eccleston, J.F. Fluorescent Nucleotide Analogs: Synthesis and Applications, Meth. Enzymol. 278:363-390 (1997).
Lizardi, P.M. and Kramer, F.R., Exponential amplification of nucleic acids: new diagnostics using DNA polymerases and RNA replicases, Trends Biotechnol. 1991 9:53-8, (1991).
Kwoh et al., Transcription-based amplification system and detection of amplified human immunodeficiency virus type 1 with a bead-based sandwich hybridization format, PNAS 86:1173-7 (1989).
La Spada, et al., Androgen receptor gene mutations in X-linked spinal and bulbar muscular atrophy, Nature, 352:77-79 (1991).
Mangalam, H.J., "tacg—a grep for DNA" BMC Bioinformatics 3:8 (2002).
Mansfield et al., Nucleic acid detection using non-radioactive labelling methods, Mol. Cell. Probes 9:145-156, (1995).
Moore, D.F. and Curry, J. I., Detection and Identification of Mycobacterium tuberculosis Directly from Sputum Sediments by Ligase Chain Reaction, Journal of Clinical Microbiology, 4:1028-1031 (1998).
Rice et al., "EMBOSS: The European Molecular Biology Open Software Suite." Trends in Genetics, 6:276-7 (2000).
Saiki, "Amplification of Genomic DNA" in PCR Protocols, Innis et al., Eds., Academic Press, San Diego, CA 1990, pp. 13-20.
Verkerk et al., Identification of a Gene (FMR-1) Containing a CGG Repeat Coincident with a Breakpoint Cluster Region Exhibiting Length Variation in Fragile X Syndrome, Cell, 65:905-914 (1991).
Walker et al., Isothermal in vitro Amplification of DNA by a Restriction Enzyme/DNA Polymerase System, PNAS, 89:392-6 (1992).

(Continued)

Primary Examiner — Teresa E Strzelecka
(74) Attorney, Agent, or Firm — Foley and Lardner LLP

(57) ABSTRACT

The present invention provides methods of determining the size of a particular nucleic acid segment of interest in a sample of nucleic acids through fragmentation of DNA, size fractionation, an optional second fragmentation, and identification using a marker sequence. In particular aspects, an expansion or reduction of tandem repeat sequences can be detected. In further aspects, carriers and individuals afflicted with fragile X syndrome or other diseases associated with tandem repeats can be distinguished from normal individuals.

13 Claims, 5 Drawing Sheets

OTHER PUBLICATIONS

Wharam et al., Specific detection of DNA and RNA targets using a novel isothermal nucleic acid amplification assay based on the formation of a three-way junction structure, Nucleic Acids Res., 29:E54-E54 (2001).

Whelan et al, Direct Genotypic Detection of *Mycobacterium tuberculosis* Rifampin Resistance in Clinical Specimens by Using Single-Tube Heminested PCR, *Journal of Clinical Microbiology*, 3:556-561(1995).

Zhu, Directly labeled DNA probes using fluorescent nucleotides with different length linkers, Nucl. Acids Res. 22:3418-3422, (1994).

Petek et al., Mosaicism in a fragile X male including a de novo deletion in the *FMR1* gene. American Journal of Medical Genetics, 84:229-232, 1999.

International Search Report for PCT Patent Application No. PCT/US2007/008985.

Brown et al., Rapid fragile X carrier screening and prenatal diagnosis using a nonradioactive PCR test. JAMA, 270 (13): 1569-1575, 1993.

Ciotti et al., Triplet repeat primed PCR (TP PCR) in molecular diagnostic testing for Friedreich Ataxia. Journal of Molecular Diagnostics, 6(4): 285-289, 2004.

Dahl et al., A Homogeneous assay for analysis of FMR1 promoter methylation in patients with fragile X syndrome. Clinical Chemistry, 53(3): 1-3, 2007.

Daniels et al., Single-cell analysis of unstable genes. Journal of Assisted Reproduction and Genetics, 13(2): 163-169, 1996.

Erster et al., Polymerase chain reaction analysis of fragile X mutations. Human Genetics, 90: 55-61, 1992.

Falk et al., Simple procedure for automatic detection of unstable Alleles in the myotonic dystrophy and Huntington's disease Loci. Genetic Testing, 10(2): 2006.

Khaniani et al., An improved diagnostic PCR assay for identification of cryptic heterozygosity for GCC triplet repeat alleles in the Fragile X gene (FMR1). Molecular Cytogenetics, 1(5): 1-6, 2008.

Muglia et al., Nonisotopic method for accurate detection of $(CAG)_n$ repeats causing Huntington disease. Clinical Chemistry, 42(10): 1601-1603, 1996.

Pergolizzi et al., Detection of full fragile X mutation. The Lancet, 339: 271-272, 1992.

Saluto et al., An enhanced polymerase chain reaction assay to detect pre- and full mutation alleles of the *Fragile X Mental Retardation 1 gene*. Journal of Molecular Diagnostics, 7(5): 605-612, 2005.

Snow et al., Analysis of a CGG sequence at the FMR-1 locus in fragile X families and in the general population. Am. J. Hum. Genet., 53: 1217-1228, 1993.

Strelnikov et al., A simple multiplex FRAXA, FRAXE, and FRAXF PCR assay convenient for wide screening programs. Human Mutation, 13: 166-169, 1999.

Tassone et al., A rapid polymerase chain reaction-based screening method for identification of all-expended alleles of the Fragile X (*FMR1*) gene in newborn and high-risk populations. Journal of Molecular Diagnostics, 10(1): 43-49, 2008.

Warner et al., A general method for the detection of large CAG repeat expansions by fluorescent PCR. J. Med. Genet., 33:1022-1026, 1996.

Zhou et al., Robust fragile X $(CGG)_n$ genotype classification using a methylation specific triple PCR assay. J. Med. Genet., 41: 1-8, 2004.

Zhou et al., Simplified molecular diagnosis of fragile X syndrome by florescent methylation-specific PCR and GeneScan analysis. Clinical Chemistry, 52(8), 1492-1500, 2006.

European Search Report dated Jan. 18, 2010 for EP Application No. 07755301.4.

Hunter et al, Verification of somatic CAG repeat expansion by pre-PCR fractionation, Journal of Neuroscience Methods, Elsevier Publisher B.V., Amsterdam, NL, 144(1):11-17, 2005.

Office Action dated Aug. 31, 2011 for CN Application No. 200780045172.9.

Non-final Office Action dated Dec. 30, 2011 for U.S. Appl. No. 12/444,361.

Findlay et al., Rapid trisomy diagnosis (21, 18 and 13) using fluorescent PCR and short tandem repeats: Applications for prenatal diagnosis and preimplantation genetic diagnosis. Journal of Assisted Reproduction and Genetics, 15(5): 266-275, 1998.

\* cited by examiner

CTCCGTTTCGGTTTCACTTCCGGTGGAGGGCCGCCTCTGAGCGGGCGGCGGGCCGACGGCGA
GCGCGGGCGGCGGCGGTGACGGAGCCGCCGCTGCCAGGGGGCGTGCGGCAGCGCGGCGGCGG
CGGCGGCGGCGGCGGCGGCGGAGGCGGCGGCGGCGGCGGCGGCGGCGGCTGGGCCTCGA
GCGCCCGCAGCCCACCTCTCGGGGGCGGGCTCCCGGCGCTAGCAGGGCTGAAGAGAAGATGG
AGGAG

FIGURE 2

CTCCAGTCCTGTGATCCGGGCCCGCCCCCTAGCGGCCGGGGAGGGAGGGGCCGGGTCCGCGG
CCGGCGAACGGGGCTCGAAGGGTCCTTGTAGCCGGGAATGCTGCTGCTGCTGCTGCTGCTGC
TGCTGCTGCTGCTGCTGCTGCTGCTGCTGCTGGGGGGATCACAGACCATTTCTTTC
TTTCGGCCAGGCTGAGGCCCTGACGTGGATGGGCAAACTGCAGGCCTGGGAAGGCAGCAAGC
CGGGCCGTCCGTGTTCCATCCTCCACGCACCCCACCTATCGTTGGTTCGCAAAGTGCAAAG

FIGURE 3

AGGCCTAGGAAGGTGGATCACCTGAGGTCCGGAGTTCAAGACTAACCTGGCCAACATGGTGA
AACCCAGTATCTACTAAAAATACAAAAAAAAAAAAAAAGAAGAAGAAGAAGAAGAAAATA
AAGAAAAGTTAGCCGGGCGTGGTGTCGCGCGCCTGTAATCCCAG

FIGURE 4

NUCLEIC ACID SIZE DETECTION METHOD

FIELD OF THE INVENTION

The present invention relates generally to the field of medical diagnostics. In particular, the present invention relates to methods of detecting genetic mutations characterized by an expansion of tandem repeats.

BACKGROUND

A tandem repeat in DNA represents two or more contiguous approximate copies of a pattern of nucleotides. Tandem repeats have been shown to be associated cause a variety of human diseases. Dramatic expansion of trinucleotide repeats has been associated with such diseases as fragile-X mental retardation (see Verkerk, et al., (1991) Cell, 65, 905-914), Huntington's disease (see Huntington's Disease Collaborative Research Group. (1993) Cell, 72, 971-983), myotonic dystrophy (see Fu, et al., (1992) Science, 255, 1256-1258), spinal and bulbar muscular atrophy (see La Spada, et al., (1991) Nature, 352, 77-79) and Friedreich's ataxia (see Campuzano, et al., (1996) Science, 271, 1423-1427).

Fragile X syndrome is one of the most common causes of inherited mental retardation, occurring in approximately one in 1,250 males and approximately one in 2,500 females. Males with fragile X syndrome typically exhibit some degree of mental impairment, ranging from learning disabilities to mental retardation to autism. Characteristic physical features (e.g., enlarged ears, elongated face with prominent chin), connective tissue problems (e.g., mitral valve prolapse, and double-jointed fingers), and characteristic behaviors (e.g., attention deficit disorders, speech disturbances, and unusual responses to various touch, auditory, or visual stimuli) may also be exhibited. Affected females present with similar but milder mental impairment, physical characteristics, and behavioral characteristics as those of affected males.

The mutation responsible for fragile X syndrome involves expansion of a trinucleotide (CGG) tandem repeat sequence located in the 5' untranslated region of the FMR1 gene on the X chromosome. The number of CGG repeats in the FMR1 gene determines whether an individual is normal or has one of the two categories of mutation: premutation (carriers) and full mutation (affected individuals). The number of repeats ranges from less than 55 repeats in normal, non-carrier individuals, whereas premutation consists of 55 to 200 repeats and full mutation consists of more than 200 repeats (Chen et al. Hum. Mol. Genetics 12(23):3067-74, 2003).

Both males and females carrying a premutation in one gene are unaffected. Male carriers are referred to as "normal transmitting" males, and pass on the mutation, relatively unchanged in size to each daughter. Although such daughters are unaffected, they are at risk of having affected offspring because a premutation is susceptible to expansion after passage through a female meiosis. Furthermore, the larger the premutation, the higher the risk of expansion to a full mutation in any offspring.

Most males with a full mutation exhibit mental retardation and stereotypical physical and behavioral characteristics. For females with a full mutation, about one-third exhibit normal intelligence, about one-third exhibit borderline intelligence, and about one-third exhibit mental retardation.

Currently, the industry standard for screening carriers or diseased individuals with expansion of tandem repeat regions such as Fragile X is a combination of direct PCR amplification of the CGG repeat and analysis by Southern blotting.

SUMMARY OF THE INVENTION

In one aspect of the invention, there are provided methods of determining the size of a particular nucleic acid segment of interest in a sample of nucleic acids. This method is accomplished by fragmenting the nucleic acid in the sample into fragments, wherein the segment is associated with a marker sequence in the fragment, separating the fragments into fractions according to size under conditions in which the fragment(s) containing the segment will be located in the fractions according to the size of the segment, and identifying those fraction(s) containing the segment by detecting the marker sequence, wherein the size of the segment is determined by the fraction in which it is identified.

This method is applicable to essentially any nucleic acid segment of interest, however the method is particularly amenable to determining the size of nucleic acid segments which are, for example, difficult to size by direct PCR and electrophoresis. Examples include nucleic acid segments having high content of the bases guanine and cytidine, large segments of nucleic acid or segments having large numbers of tandem repeats. In a preferred embodiment, the particular nucleic acid segment of interest is a tandem repeat nucleic acid sequence.

In another aspects, invention methods are used to determine the size of a particular nucleic acid segment in a sample from an individual, thereby determining if that individual has an abnormality in size of that particular nucleic acid segment, wherein the abnormality is due to a duplication, addition, or deletion in the particular nucleic acid segment.

In still another aspect, the invention provides a method of detecting a mutation in a tandem repeat segment of a gene in a nucleic acid sample, wherein the mutation is characterized by an increase in the number of repeats compared to the number of repeats in the wild type allele. The method is accomplished by fragmenting the nucleic acid in the sample into fragments in which the tandem repeat segment is associated with a marker sequence in the fragment separating the fragments into fractions according to size under conditions in which the fragment(s) containing the tandem repeat segment will be located in the fractions according to the number of repeats in the tandem repeat segment, and identifying those fraction(s) containing the segment by detecting the marker sequence. The number of repeats in the tandem repeat segment is determined by the fraction in which it is identified. The number of repeats is compared to the number in the corresponding wild type allele, wherein a number of repeats greater that the number in wild type allele is indicative of a mutation.

In certain embodiments, the above aspect of the invention further includes determining if a mutation is a premutation or a full mutation. This determination is accomplished by comparing the number of repeats in the tandem repeat segment from the nucleic acid sample to the number in the corresponding full mutation allele, wherein a number of repeats greater than the wild type allele but less than the full mutation is indicative of a premutation allele, and a number of repeats greater than or equal to the full mutation is indicative of a full mutation allele. In other embodiments the number of repeats in the tandem repeat region of the nucleic acid sample can be compared to the number of repeats found in each of a wild type allele, a premutation allele, and a full mutation allele.

In other aspects, there are provided methods for detecting carriers of genetic mutations characterized by the expansion or reduction of a tandem repeat segment of a gene and diagnosing individuals afflicted with diseases caused by such an expansion. The method involves the detection of wild type alleles, premutation alleles and/or full mutation alleles for a particular gene as described above. A genotype may then be determined based on the allele(s) present in an individual, allowing the designation of normal, carrier, or affected status.

In some embodiments of the above aspect of the invention, individuals afflicted with Fragile X syndrome (full mutation) can be distinguished from individuals that are carriers (premutation) or from those that are normal. A nucleic acid sample from the individual is fragmented to produce nucleic acid fragments in which the tandem repeat segment of the FMR1 gene is associated with a marker sequence in a fragment. The fragments are separated into fractions according to size under conditions in which the fragment(s) containing the tandem repeat segment will be located in the fractions according to the number of repeats in the tandem repeat segment, and identifying those fraction(s) containing the segment by detecting the marker sequence. The fractions are chosen so that the first fraction corresponds to tandem repeat regions having less than 55 repeats (i.e., a normal allele), the second corresponds to tandem repeat regions having 55-200 repeats (i.e, a premutation allele), and the third corresponds to tandem repeat regions having greater than 200 repeats (full mutation allele). A positive result in only one fraction indicates the individual is homozygous for the allele collected in that fraction. If only the first fraction is positive, the individual is normal; if only the second fraction is positive, the individual is a carrier; if only the third fraction is positive, the individual is affected with fragile X. A positive result more than one fraction indicates a heterozygote. If the first and the second fractions are positive, the individual is a carrier; if the first and third fractions are positive the individual is affected.

In a preferred embodiment of the above aspect of the invention, a sample containing genomic DNA is assayed for an expansion in the tandem repeat region of the FMR1 gene. Thus, genomic samples are subjected to nucleic acid fragmentation and the resulting nucleic acid fragments are separated by size into fractions. A marker sequence upstream or downstream of the tandem repeat region of the FMR1 gene, which is associated with the tandem repeat region in the fragmented nucleic acid, is amplified by polymerase chain reaction. In some embodiments the amplification of the marker sequence and detection of the amplicon is done using the TaqMan® system. In other embodiments the marker sequence is amplified and using a labeled primer and the resulting labeled amplicon is detected using capillary electrophoresis with the tandem repeat region in the fragmented nucleic acid, is amplified by polymerase chain reaction. In some embodiments the amplification of the marker sequence and detection of the amplicon is done using the TaqMan system. In other embodiments the marker sequence is amplified and using a labeled primer and the resulting labeled amplicon is detected using capillary electrophoresis.

One of skill in the art would readily recognize that the separation of fragments into fractions by size can be modified so that the fractions correspond to either a normal number of tandem repeats or an abnormal number of tandem repeats. In some embodiments, the fragmented nucleic acid may be separated by size into two fractions, an upper fraction of larger size fragments and a lower fraction of smaller size fragments. In this approach, the fractions are designed such that fragments from nucleic acid containing a normal number of tandem repeats will be found in the lower fraction while fragments from nucleic acid containing an abnormally increased number of tandem repeats will be found in the upper fraction. In other embodiments, the fragmented DNA may be separated into any number of fractions. In some embodiment the fragmented DNA may be separated into a number of fractions selected from the group consisting of 2-16, preferably 3 fractions, or 4 fractions, or 5 fractions, or 6 fractions, or 8 fractions, or even 16 fractions.

In a preferred embodiment of the above method, the fragmented DNA is separated into lower and upper fractions, wherein the lower fraction corresponds to a tandem repeat region containing less than 55 repeats (normal number of repeats) and an upper fraction containing 55 or more tandem repeats (permutation and full mutation). A normal allele can therefore be distinguished from a premutation or a full mutation.

In another preferred embodiment of the above method, the fragmented DNA is separated into three fractions, wherein a first fraction corresponds to a tandem repeat region of a normal allele (i.e., less than 55 repeats), a second fraction corresponds to a tandem repeat region of a premutation allele (i.e. 55-200 repeats), a third fraction corresponds to a tandem repeat region of a full mutation allele (i.e., greater than 200 repeats).

In yet another preferred embodiment of the above method, the fragmented DNA is separated into four fractions, wherein a first fraction corresponds to a tandem repeat region of a normal allele, a second fraction corresponds to a tandem repeat region of a small premutation allele, a third fraction corresponds to a tandem repeat region of a large premutation allele, and a fourth fraction corresponds to a tandem repeat region of a full mutation allele. In particular embodiments, the first fraction corresponds to 0-60 repeats; preferably the second fraction corresponds to 60-200 repeats; preferably the third fraction corresponds to 200-2000 repeats; and preferably the fourth fraction corresponds to 2000+ repeats. In another embodiment, the DNA is fragmented with BlpI and MlyI and fractionated such that the first fraction corresponds to 6-62 repeats; preferably the second fraction corresponds to 63-140 repeats; preferably the third fraction corresponds to 141-220 repeats; and preferably the fourth fraction corresponds to 221-2000+ repeats. In another embodiment, the DNA is fragmented with AluI and fractionated such that the first fraction corresponds to 6-68 repeats; preferably the second fraction corresponds to 69-102 repeats; preferably the third fraction corresponds to 102-202 repeats; and preferably the fourth fraction corresponds to 203+ repeats. In yet another embodiment, the DNA is fragmented with SphI and BmtI and fractionated such that the first fraction corresponds to 6-62 repeats; preferably the second fraction corresponds to 63-163 repeats; preferably the third fraction corresponds to 164-196 repeats; and preferably the fourth fraction corresponds to 197+ repeats.

Also provided are methods of estimating the number of tandem repeats in a sample of genomic DNA. In this method, test samples containing genomic DNA are subjected to nucleic acid fragmentation. The resulting nucleic acid fragments are separated by size into three or more size range fractions, and fragments containing tandem repeat segments in the various fractions are identified by detecting a marker sequence flanking the tandem repeat segment, which is associated with the tandem repeat region in the fragmented nucleic acid. The size of the tandem repeat region detected is then determined by relating the fraction size containing the repeat to the size of a tandem repeat segment present in such nucleic acid fragments. Separation into three or more size range fractions allows a finer estimation of the number of tandem repeats. In the case of fragile X, the extent of the expansion of a premutation or full mutation can be assessed.

In preferred embodiments of the above aspects of the invention, the method includes a second nucleic acid fragmentation. Preferably the second fragmentation occurs after the size separation, which follows the first nucleic acid fragmentation; preferably the second fragmentation is by restriction enzyme digestion. In more preferred embodiments, the second fragmentation separates the tandem repeat segment from a marker sequence flanking the tandem repeat segment. Preferably the second nucleic acid fragmentation does not cleave within the marker sequence.

In some embodiments of the above aspects of invention, the marker sequence is detected by amplification of all or a portion of the marker sequence and detection of the amplicon. In preferred embodiments, the marker sequence is amplified by PCR and the amplicon is detected by electrophoresis. In more preferred embodiments, a primer used in the PCR amplification reaction comprises a label, thereby labeling the resulting amplicon. The so-labeled amplicon can then be detected by methods such as capillary electrophoresis.

In other embodiments of the above aspects of the invention, the marker sequence is detected using real time PCR methods such as the TaqMan® system. In this approach a probe is used to detect the amplified region of the marker sequence.

In still other embodiments of the above aspects of the invention, the marker sequence need not be amplified and can be detected directly by hybridization to two differentially labeled oligonucleotide probes. The two probes, which hybridize to distinct segments of a marker sequence, such that both probes can bind simultaneously, are contacted with the fragmented nucleic acids under hybridization conditions. The simultaneous detection of differentially labeled probes hybridized to fragments of nucleic acids in the fractions indicates the presence of a tandem repeat region in a fragment contained in that fraction. The two oligonucleotide probes of this embodiment may be designed to hybridize to marker sequence upstream or downstream of the tandem repeat. These sequences may be adjoining the tandem repeat region or may be a distance upstream or downstream. In preferred embodiments, the marker sequences are within 500 bases upstream or downstream of the tandem repeat region; in more preferred embodiments the marker sequences are within 250 bases upstream or downstream of the tandem repeat region; in most preferred embodiments the marker sequences are within 100 bases upstream or downstream of the tandem repeat region. The probes may be designed to hybridize to the same or to opposite strands of a double-stranded marker sequence. The probes may both hybridize upstream or both downstream of the tandem repeat. Alternatively, one probe may hybridize upstream of the tandem repeats whereas the other probe hybridizes downstream.

In another aspect of the invention, there are provided methods of determining the size of a particular nucleic acid segment in a sample of nucleic acids, wherein size is determined using information obtained using a direct and an indirect method. Thus, the method comprises measuring the size of a tandem repeat segment by a direct method, measuring the size by the indirect method, and using the information obtained by the direct and indirect methods to determine the size of the tandem repeat region. In some embodiments, the direct method includes an amplification of the tandem repeat region, preferably the amplification is by PCR. In preferred embodiments, the PCR amplification includes a labeled primer. In other preferred embodiments the amplicon is subjected to electrophoresis, preferably capillary electrophoresis, and the size of the amplicon is determined by comparison to a standard run in parallel. In other embodiments the direct method includes Southern blotting. In preferred embodiments the indirect method comprises, fragmenting the nucleic acids of the sample, separating the fragmented nucleic acids into fractions according to size, and detecting a marker sequence upstream or downstream of the particular nucleic acid segment of interest, wherein the marker sequence is associated with the particular nucleic acid segment of interest in the fragmented nucleic acid. The size of the particular nucleic acid segment of interest is then determined by relating the fraction size containing the particular nucleic acid segment to the size of the particular nucleic acid segment in the sample of nucleic acids. In certain embodiments, the direct method is used as an initial screen and samples for which the size of the particular nucleic acid segment is unable to be determined by this method are further analyzed by the indirect methods. In other embodiments, sizing by direct methods is used to confirm the results of the sizing by indirect methods. In still other embodiments, sizing by direct methods is used for finely determining the size of the particular nucleic acid fragment.

In another aspect of the invention there are provided primers for amplification of marker sequences flanking the tandem repeat region of the FMR1 gene. In particular embodiments, the primers are selected from the group consisting of SEQ ID NOs:4-9

In yet another aspect of the invention, there are provided kits for detecting the size of a particular nucleic acid segment in a sample comprising a primer pair for amplifying a marker nucleotide sequence upstream or downstream of the particular nucleic acid segment, and one or more restriction endonucleases for cleaving the nucleic acid sample to generate a fragment of the nucleic acid sample which contains the particular nucleic acid segment and the upstream or downstream marker sequence. In certain embodiments the kit further comprises one or more restriction endonucleases for cleaving the particular nucleic acid segment from the marker nucleotide sequence. In still other embodiments, the kit may further contain one or more controls for verifying proper size separation of fragments; preferably the control consists of one or more primer pairs that are used to amplify one or more control fragments from the size-separated nucleic acid sample. In further embodiments, the kit may further contain one or more controls for verifying the completion of the one or more enzyme digests; preferably the control consists of on or more primer pairs designed to amplify a control fragment that includes a recognition site for the enzyme used. The kit may further contain any necessary buffers or other reagents.

In preferred embodiments of the above aspect of the invention, the particular nucleic acid segment contains a tandem repeat segment. In more preferred embodiments, the kit is for the detection of the tandem repeat segment of the FMR1 gene; preferably the enzyme for generating fragments of the nucleic acid sample is AluI; preferably the enzyme for cleaving the marker sequence from the tandem repeat is BstNI; preferably the kit contains one or more control primers pairs to determine if enzyme digestions are completed; preferably the kit contains one or more primer pairs to detect the presence of one or more control fragments in the size-separated nucleic acid sample. In other preferred embodiments, the kit is for the detection of the tandem repeat segment of the FMR1 gene; preferably the enzymes for generating fragments of the nucleic acid sample are BlpI and MlyI; preferably the enzyme for cleaving the marker sequence from the tandem repeat is BmtI; preferably the kit contains one or more control primers pairs to determine if enzyme digestions are completed; preferably the kit contains one or more primer pairs to detect the presence of one or more control fragments in the size-separated nucleic acid sample. In still other preferred embodiments, the kit is for the detection of the tandem repeat segment of the FMR1 gene; preferably the enzymes for generating fragments of the nucleic acid sample are SphI and BmtI; preferably the enzyme for cleaving the marker sequence from the tandem repeat is BstNI; preferably the kit contains one or more control primers pairs to determine if enzyme digestions are completed; preferably the kit contains one or more primer pairs to detect the presence of one or more control fragments in the size-separated nucleic acid sample.

"Segment" as used herein in reference to nucleic acid, refers to a piece of contiguous nucleic acid.

"Particular nucleic acid segment of interest" as used herein refers to a specific "segment" or piece of nucleic acid having a known sequence, preferred segments are those segments that are difficult to amplify by PCR. Examples include nucleic acid segments having high content of the bases guanine and cytidine, large segments of nucleic acid or segments having large numbers of tandem repeats, generally more than 100 tri-nucleotide repeats. In some embodiments the segment comprises a deletion, a duplication or an insertion. In a preferred embodiment, the particular nucleic acid segment of interest comprises a tandem repeat region.

"Size" as used in reference to a particular nucleic acid segment of interest refers to quantity or amount that describes the magnitude of that segment and can be represented by, for example, molecular weight, number of base pairs, or number of copies of a tandem repeat.

"Fragment" as used herein refers to a portion of nucleic acid resulting from a process in which longer lengths of nucleic acid are broken up into shorter lengths of nucleic acid. Nucleic acids may be broken up or fragmented by chemical or biochemical means, preferably nucleic acids are fragmented in a manner that is reproducible, preferably nucleic acids are fragmented by one or more restriction endonucleases. Preferably nucleic acids are fragmented so that the particular nucleic acid segment of interest and its associated marker sequence are located on the same fragment. The length of a fragment containing the nucleic acid segment of interest will depend on the length of the nucleic acid segment of interest as well as the restriction enzyme chosen to fragment the DNA. Thus, the length of the of the fragment includes the nucleic acid segment of interest plus the region upstream of the segment to the 5' restriction enzyme recognition site (i.e., the 5' end of the fragment) and the region downstream of the segment region to the 3' restriction enzyme recognition site (i.e., the 3' end of the fragment).

"Separating fragments" as used herein refers to the process whereby the fragments contained in a mixture of different fragments are physically separated from one another.

"Fractionation" as used herein refers to a process whereby a single mixture of individual components is processed so that at least some of the individual components in the mixture become separated from each other. For example, chromatography is a fractionation method that separates a mixture of components based on some physical/chemical principle. The components may be separated in a gel or on a membrane so that the individual components may be separately identified. The individual components of a mixture may be fractionated by separating the mixture into the different components which are captured in separate aliquots of liquid (i.e. fractions). As used herein "fraction" in the context of the invention refers to a collection of fragments having a certain size or range of sizes that differs from the size or range of sizes of the starting non-fractionated mixture of fragments.

"Identifying those fractions containing the segment" as used herein means that the fraction of size-separated fragments that contains the segment of interest, is determined by the detection of a marker sequence associated with that segment on a fragment of nucleic acid.

The phrase "tandem repeat region" or "tandem repeat segment" as used herein refers to a region of DNA that contains a multiple copies of a short sequence of DNA. "Tandem repeat sequences" or "tandem repeats" or simply "repeats" are used interchangeably herein and refers to the short sequence of DNA that is repeated in the tandem repeat region. Such tandem repeats can lie adjacent to each other in the same orientation (i.e., direct tandem repeats) or in the opposite direction to each other (i.e., inverted tandem repeats). The repeated sequences may be di-, tri-, tetra-, or more nucleotides in length. Expansion the number of copies of the tandem repeat sequences within the coding or noncoding regions of some human genes is associated with repeat expansion disease.

As used herein, the term "sample" or "test sample" refers to any liquid or solid material containing genomic DNA. In preferred embodiments, a test sample is obtained from a biological source (i.e., a "biological sample"), such as cells in culture or a tissue sample from an animal, most preferably, a human. Preferred sample tissues include, but are not limited to, blood, bone marrow, body fluids, cerebrospinal fluid, plasma, serum, or tissue (e.g. biopsy material).

As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, reverse transcribed from sample DNA or RNA).

"Target nucleic acid" as used herein refers to segments of a chromosome, a complete gene with or without intergenic sequence, segments or portions a gene with our without intergenic sequence, or sequence of nucleic acids to which probes or primers are designed. Target nucleic acids may include wild type sequences, nucleic acid sequences containing mutations, deletions or duplications, tandem repeat regions, a gene of interest, a region of a gene of interest or any upstream or downstream region thereof. Target nucleic acids may represent alternative sequences or alleles of a particular gene. Target nucleic acids may be derived from genomic DNA, cDNA, or RNA. As used herein target nucleic acid may be native DNA or a PCR amplified product.

The term "marker sequence" as used herein refers to a segment of nucleic acid which is associated with a nucleic acid segment of interest so that detection of the marker sequence in a sample is indicative of the presence of the nucleic acid segment of interest. The marker sequence for detecting a particular nucleic acid segment of interest should be selected on the basis that the marker is uniquely or substantially associated with the nucleic acid segment of interest in fragments present in a particular size fraction. Marker sequences can be detected by nucleic acid amplification using primer based hybridization methods. Marker sequences can also be detected by hybridization to one or more nucleic acid probe(s). In accordance with the methods disclosed herein, a fragment containing a tandem repeat segment is identified in size fractioned nucleic acid fragments by detecting a marker sequence that is either upstream or downstream of the tandem repeat.

Marker sequences may be within the nucleic acid segment of interest or may be flanking the nucleic acid of interest. The term "flanking" as used herein refers to a region of DNA either adjoining or a distance from a region of interest. The flanking region may be "upstream" (i.e., 5') or "downstream" (i.e., 3') of the region of interest. The marker sequence may be adjoining the tandem repeat region or may be located a distance upstream or downstream. In preferred embodiments, the marker sequence is within 500 bases upstream or downstream of the tandem repeat region; in more preferred embodiments the marker sequence is within 250 bases upstream or downstream of the tandem repeat region; in most preferred embodiments the marker sequence is within 100 bases upstream or downstream of the tandem repeat region. The flanking region may be coding or non-coding sequence and may be the same or a different gene as the gene comprising the region of interest. In preferred embodiments, the marker sequence is flanking the nucleic acid segment of interest.

In certain embodiments, the size of the particular nucleic acid segment of interest is determined by relating the fraction size containing the particular nucleic acid segment to the size of the particular nucleic acid segment in the sample of nucleic acids. This step of relating the fraction size containing the particular nucleic acid segment to the size of the particular nucleic acid segment in the sample of nucleic acids can be accomplished using a look-up table as disclosed herein. In other embodiments this step is accomplished with a computer program.

The phrase "relating the fraction size containing the particular nucleic acid segment of interest to the size of the particular nucleic acid segment of interest that would be present in that fraction under the conditions which generated the fragment" as used herein refers to the means by which the size of the particular nucleic acid segment of interest is determined from its location in a particular fraction size. In one approach, a look-up table is established for each combination of particular nucleic acid segment of interest and fragmentation approach (e.g. particular restriction endonuclease(s) used). The look-up table links each fraction (containing a range of fragment sizes) to the length of the segment of interest that is present in such fragments. In any particular fraction, there are fragments that contain the segment of interest and other sequence. Thus, in any fraction, one can calculate from sequence data the number of bases in the fragments that represent the segment of interest. This correlation may be established experimentally or by using known DNA sequence for the fragments generated. For any particular unknown sample, the size of a segment of interest can be determined by relating the fragment size that contains the segment of interest to the appropriate look-up table reflecting the same conditions for fragment generation. By using this process one relates the fraction size containing the particular nucleic acid segment of interest to the size of the particular nucleic acid segment of interest that would be present in the fraction under the conditions which generated the fragment. It is not essential that one prepare a look-up table to perform the method. For example, one could generate a computer program to perform the relating step.

"Genomic nucleic acid" or "genomic DNA" refers to some or all of the DNA from the nucleus of a cell. Genomic DNA may be intact or fragmented (e.g., digested with restriction endonucleases by methods known in the art). In some embodiments, genomic DNA may include sequence from all or a portion of a single gene or from multiple genes, sequence from one or more chromosomes, or sequence from all chromosomes of a cell. In contrast, the term "total genomic nucleic acid" is used herein to refer to the full complement of DNA contained in the genome of a cell. As is well known, genomic nucleic acid includes gene coding regions, introns, 5' and 3' untranslated regions, 5' and 3' flanking DNA and structural segments such as telemetric and centromeric DNA, replication origins, and intergenic DNA. Genomic nucleic acid may be obtained from the nucleus of a cell, or recombinantly produced. Genomic DNA also may be transcribed from DNA or RNA isolated directly from a cell nucleus. PCR amplification also may be used. Methods of purifying DNA and/or RNA from a variety of samples are well-known in the art.

The terms "allele" and "allelic variant" are used interchangeably herein. An allele is any one of a number of alternative forms or sequences of the same gene occupying a given locus or position on a chromosome. A single allele for each locus is inherited separately from each parent, resulting in two alleles for each gene. An individual having two copies of the same allele of a particular gene is homozygous at that locus whereas an individual having two different alleles of a particular gene is heterozygous.

"Repeat expansion disease" refers to any of about two dozen human diseases displaying Mendelian inheritance patterns shown to be caused by expansions of intrinsically polymorphic tandem repeats, mainly involving different trinucleotide motifs but also longer repetitive sequences up to 12-mers (Table 1). A characteristic of an allele containing an expanded tandem repeat is an excessive instability in successive generations (dynamic mutations). Furthermore, these alleles can differ in lengths among cell populations of the same organism (mosaicism). One type of repeat expansion disease is the trinucleotide repeat disorders (e.g., fragile X syndrome, myotonic dystrophy 1, etc.), the most abundant form of repeat expansion diseases. These diseases exhibit intergenerational repeat instability with a tendency towards further expansion of the tandem repeat. Increased repeat lengths in successive generations can lead to an earlier age of onset in affected individuals and/or an accentuation of clinical symptoms. The methods of measuring tandem repeat length as described herein can be applied to measures tandem repeat length for any of the diseases/genes in Table 3.

TABLE 1

Exemplary tandem repeat expansion diseases

| Disease (gene designation) | Protein | Tandem repeat sequence | Repeat Localization | Normal repeat range | Expanded repeat |
|---|---|---|---|---|---|
| Dentatorubral-pallidoluysian atrophy (DRPLA) | atrophin-1 | CAG | coding | 6-35 | 49-88 |
| Progressive myoclonus epilepsy (EPM1)# | CSTB | CCCCGCCCCGCG (SEQ ID NO: 39) | 5' UTR | 2-3 | 50-80 |
| Fragile XA-syndrome (FRAXA)* | FMR1 | CGG | 5' UTR | 6-53 | >230 |

TABLE 1-continued

Exemplary tandem repeat expansion diseases

| Disease (gene designation) | Protein | Tandem repeat sequence | Repeat Localization | Normal repeat range | Expanded repeat |
|---|---|---|---|---|---|
| Fragile XE-syndrome (FMR1)* | FMR-2 | GCC | 5' UTR | 6-35 | >200 |
| Friedreich ataxia (FRDA)# | Frataxin | GAA | intronic | 7-34 | >100 |
| Huntington disease (huntingtin) | huntingtin | CAG | coding | 4-35 | 36-250 |
| Huntington disease-like 2 (JPH-3) | junctophilin-3 | CTG | coding | 6-27 | >40-60 |
| Spinobulbar musc. atrophy, Kennedy disease (AR)* | androgen rec. | CAG | coding | 9-36 | 38-62 |
| Myotonic dystrophy 1 (DM1) | DMPK/SIX5 | CTG | 3' UTR | 5-37 | >50 |
| Myotonic dystrophy 2 (DM2) | ZNF9 | CCTG | intronic | 10-26 | 75->11000 |
| Spinocerebellar ataxia 1 (SCA1) | ataxin-1 | CAG | coding | 6-44 | 39-82 |
| Spinocerebellar ataxia 2 (SCA2) | ataxin-2 | CAG | coding | 15-31 | 36-63 |
| Spinocerebellar ataxia 3, Machado-Joseph disease (SCA3) | Ataxin-3 | CAG | coding | 12-40 | 55-84 |
| Spinocerebellar ataxia 6 (SCA6) | CACNA1A | CAG | coding | 4-18 | 21-33 |
| Spinocerebellar ataxia 7 (SCA7) | Ataxin-7 | CAG | coding | 4-35 | 37-306 |
| Spinocerebellar ataxia 8 (SCA8) | not known | CTG | 3' UTR | 16-37 | 110-250 |
| Spinocerebellar ataxia 10 (SCA10) | Ataxin-10 | ATTCT | intronic | 10-22 | 800-4600 |
| Spinocerebellar ataxia 12 (SCA12) | PP2A-PR55B | CAG | promotor | 7-28 | 66-78 |
| Spinocerebellar ataxia 17 (SCA17) | TBP | CAG | coding | 25-42 | 47-63 |
| Oculopharyngeal muscular dystrophy (PABPN1) | PABPN1 | GCG | coding | 6 | 7-13 |
| Synpolydactyly, type II (HOXD13) | HOXD13 | GCN | coding | 15 | 22-24 |

*= X chromosome;
= autosomal recessive;
undesignated = autosomal dominant

As used herein, the term "oligonucleotide" refers to a short polymer composed of deoxyribonucleotides, ribonucleotides or any combination thereof. Oligonucleotides of the invention are generally between about 10 and about 100 nucleotides in length. Oligonucleotides are preferably 15 to 70 nucleotides long, with 20 to 26 nucleotides being the most common. The single letter code for nucleotides is as described in the U.S. Patent Office Manual of Patent Examining Procedure, section 2422, table 1. In this regard, the nucleotide designation "R" means guanine or adenine, "Y" means thymine (uracil if RNA) or cytosine; and "M" means adenine or cytosine. An oligonucleotide may be used as a primer or as a probe.

As used herein, the term "substantially purified" in reference to oligonucleotides does not require absolute purity. Instead, it represents an indication that the sequence is relatively more pure than in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

As used herein, the term "hybridize" or "specifically hybridize" refers to a process where two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target or marker sequence, positioned 3' or 5' to a contiguous sequence of bases that hybridize under stringent hybridization conditions to a target or marker sequence.

The term "complement" as used herein means the complementary sequence to a nucleic acid according to standard Watson/Crick pairing rules. A complement sequence can also be a sequence of RNA complementary to the DNA sequence or its complement sequence, and can also be a cDNA.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

The term "non-coding sequence" as used herein means a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860 passim.

As used herein, a "primer" for amplification is an oligonucleotide that specifically anneals to a target or marker nucleotide sequence. The 3' nucleotide of the primer should be identical to the target or marker sequence at a corresponding nucleotide position for optimal amplification.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

As used herein, sequences that have "high sequence identity" have identical nucleotides at least at about 50% of aligned nucleotide positions, preferably at least at about 75% of aligned nucleotide positions, more preferably at least at about 90% of aligned nucleotide positions, and most preferably at least at about 95% of aligned nucleotide positions.

As used herein "TaqMan® PCR detection system" refers to a method for real time PCR. In this method, a TaqMan® probe which hybridizes to the nucleic acid segment amplified is included in the PCR reaction mix. The TaqMan® probe comprises a donor and a quencher fluorophore on either end of the probe and in close enough proximity to each other so that the fluorescence of the donor is taken up by the quencher. However, when the probe hybridizes to the amplified segment, the 5'-exonuclease activity of the Taq polymerase cleaves the probe thereby allowing the donor fluorophore to emit fluorescence which can be detected.

BRIEF DESCRIPTION OF THE FIGURES

FIG. 2. Exemplary sequence (SEQ ID NO: 1) of a region of the FMR1 gene showing the CGG tandem repeat region (single underlining), preferred locations for hybridizing PCR primers (shaded regions), and a preferred location for a hybridizing probe (double-underlining).

FIG. 3. Exemplary sequence (SEQ ID NO:2) of the downstream 3' untranslated region of the DM-1 gene showing the CTG tandem repeat region (single underlining), preferred locations for hybridizing PCR primers (shaded regions), and a preferred location for a hybridizing probe (double-underlining).

FIG. 4. Exemplary sequence (SEQ ID NO:3) of the first intronic region of the FRDA gene showing the CAA tandem repeat region (single underlining), preferred locations for hybridizing PCR primers (shaded regions), and a preferred location for a hybridizing probe (double-underlining).

DETAILED DESCRIPTION OF THE INVENTION

Figure 1:
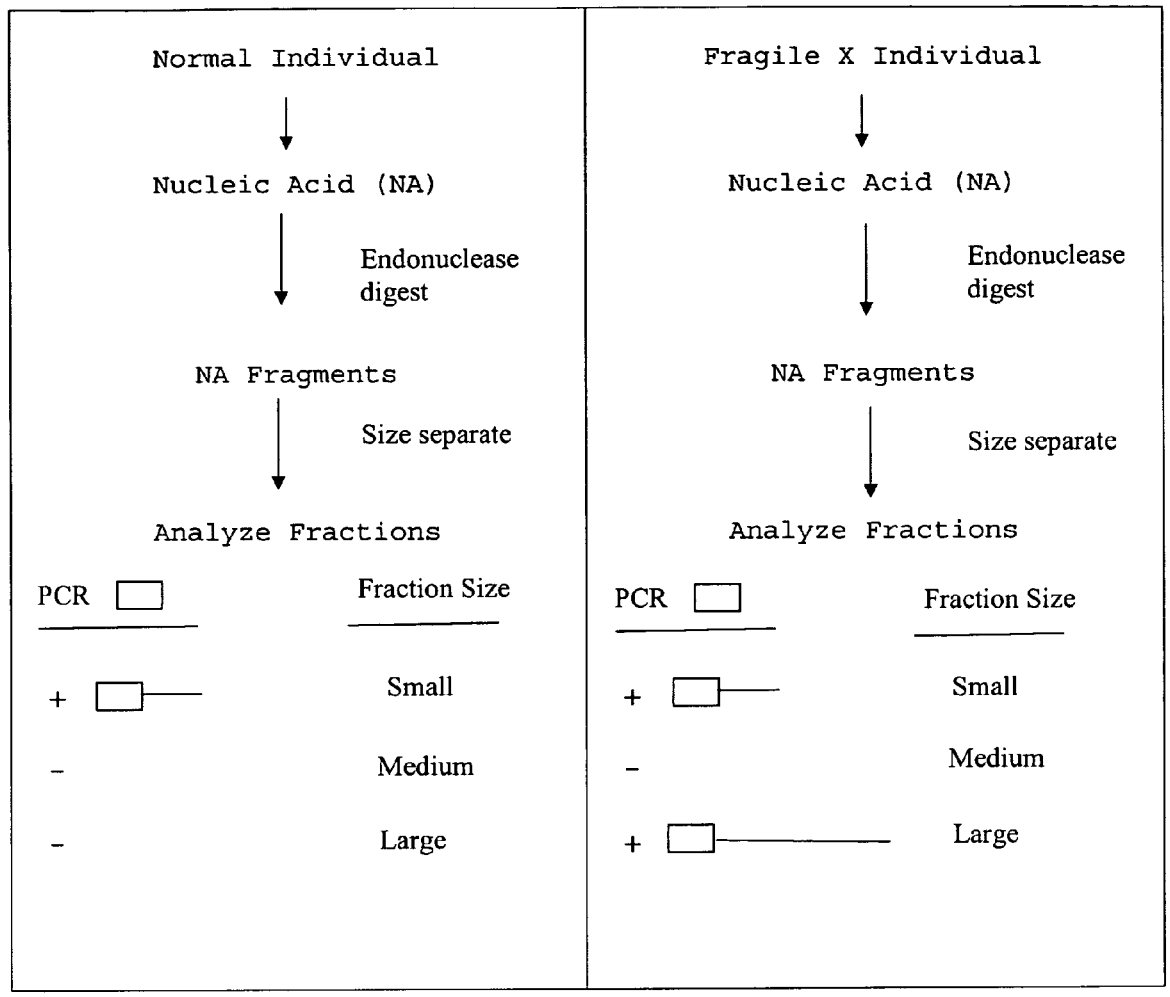
FIG. 1. A schematic showing one embodiment of the method of detecting the tandem repeats. The presence of FMR1 fragments with a particular length of tandem repeat is shown schematically at the bottom for each size fraction indicated (i.e. small, medium and large). The designation of + or − is shown below PCR to indicate whether PCR amplification of the flanking marker sequence occurs when the particular fragment is present in the fraction.
Figure 5:
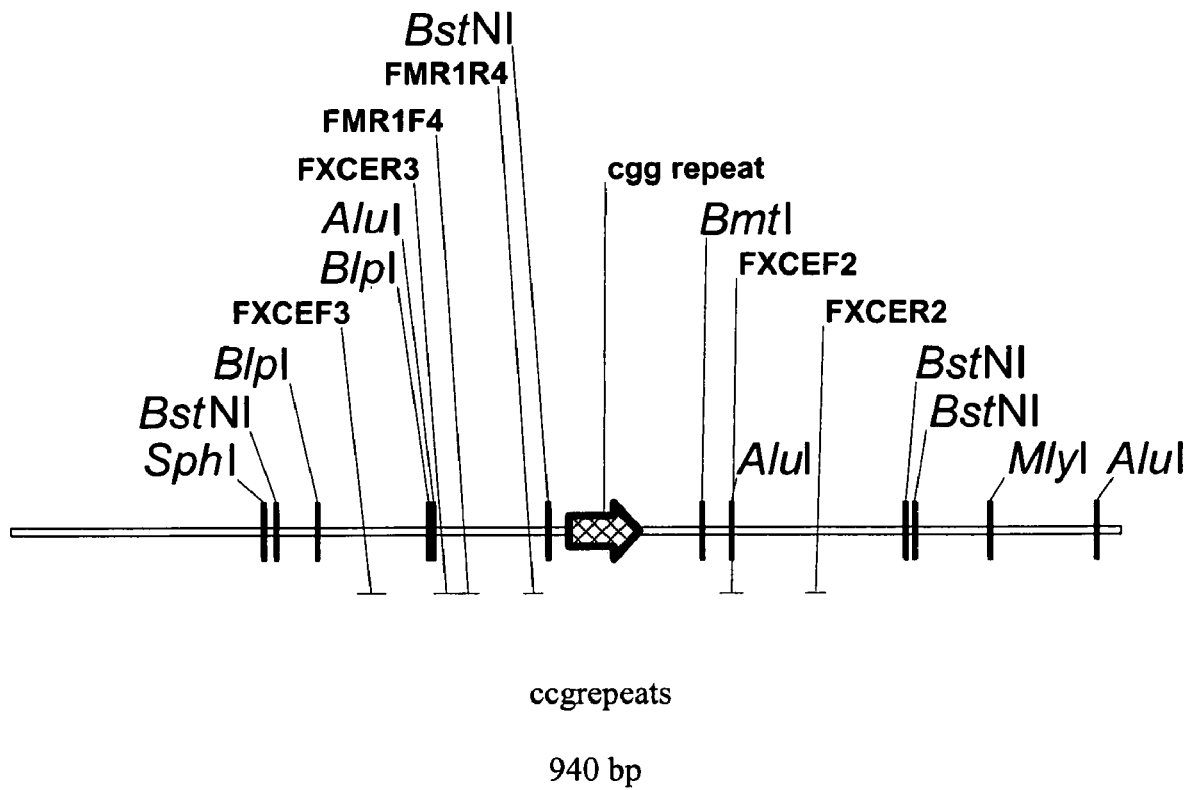
FIG. 5. Restriction enzyme map of a region of the FMR1 gene. FXCEF3, FXCER3, FMR1F4, FMR1R4, FXCEF2, and FXCER2 show the location of hybridization of preferred oligonucleotide primers. FXCEF3/FXCER3, FMR1F4/FMR1R4, and FXCEF2/FXCER2 are preferred primer pairs for amplification of marker sequences when the nucleic acid is fragmented with SphI/BmtI, AluI, and BlpI/MlyI, respectively.

In accordance with the present invention, there are provided methods of detecting a particular nucleic acid segment of interest in a sample of nucleic acids. In particular embodiments, the particular nucleic acid segment of interest is a tandem repeat and the method is used to determine information about the size of such tandem repeat. This information may be used to determine if an individual carries a genetic mutation characterized by an increase (i.e., expansion) or a decrease (i.e., reduction) in the number of tandem repeats associated with a particular gene. Thus, described is a method of measuring the size of a tandem repeat segment in a sample of nucleic acids, the method comprising identifying the tandem repeat in fractions of size-separated nucleic acid fragments by detecting a marker sequence flanking the tandem repeat segment and then relating the fraction size containing the repeat to the size of a tandem repeat segment present in such nucleic acid fragments. FIG. 1 shows one embodiment of this method in schematic form. As will be discussed, a variation of this method is to perform a second fragmentation after the size separation and prior to the "analysis" step.

Sample Preparation

The methods of the present invention can be used to detect mutations characterized by an expansion or reduction of tandem repeat region of a gene in the genomic DNA of a test sample. Therefore, the method may be performed using any biological sample containing genomic DNA. Examples include tissue samples or any cell-containing bodily fluid. Blood is the preferred biological sample. Biological samples may be obtained by standard procedures and may be used immediately or stored, under conditions appropriate for the type of biological sample, for later use.

Methods of obtaining test samples are well known to those of skill in the art and include, but are not limited to, aspirations, tissue sections, drawing of blood or other fluids, surgical or needle biopsies, and the like. The test sample may be obtained from individual or patient. The test sample may contain cells, tissues or fluid obtained from a patient suspected being afflicted with or a carrier for a disorder caused by an expansion of tandem repeat sequences. The test sample may be a cell-containing liquid or a tissue. Samples may include, but are not limited to, amniotic fluid, biopsies, blood, blood cells, bone marrow, fine needle biopsy samples, peritoneal fluid, plasma, pleural fluid, saliva, semen, serum, tissue or tissue homogenates, frozen or paraffin sections of tissue. Samples may also be processed, such as sectioning of tissues, fractionation, purification, or cellular organelle separation.

The invention methods can be used to perform prenatal diagnosis using any type of embryonic or fetal cell or nucleic acid containing body fluid. Fetal cells can be obtained through the pregnant female, or from a sample of an embryo. Thus, fetal cells are present in amniotic fluid obtained by amniocentesis, chorionic villi aspirated by syringe, percutaneous umbilical blood, a fetal skin biopsy, a blastomere from a four-cell to eight-cell stage embryo (pre-implantation), or a trophectoderm sample from a blastocyst (pre-implantation or by uterine lavage).

In particular embodiments, genomic DNA may be used. Genomic DNA may be isolated from cells or tissues using standard methods, see, e.g., Sambrook, et al., 1989, Molecular Cloning: A Laboratory Manual, Second Edition, Cold Spring Harbor Press, Plainview, N.Y.

Fragmentation of Genomic DNA

Genomic DNA may be fragmented by various methods well-known in the art. Preferably, a restriction endonuclease digestion is used to fragment the DNA.

A "restriction endonuclease" or "restriction enzyme" as used herein refers to an enzyme that cuts double-stranded DNA at a specific sequence (i.e., the recognition sequence or site). The frequency with which a given restriction endonuclease cuts DNA depends on the length of the recognition site of the enzyme. For example, some enzymes recognize sites that are four nucleotides long (referred to as "four cutters"). In general one can estimate how frequently an enzyme should cut a piece of DNA based the length of the recognition site and the assumption that the probability of any one nucleotide occurring at a given location is ¼. In the case of a "four cutter" a specific sequence of four nucleotides must be present. Assuming that each nucleotide has an equal chance (i.e., ¼) of occurring at any particular site within the four nucleotide sequence, then a four-cutter should on average cut once every 256 base pairs (i.e., ¼×¼×¼×¼=1/256). A similar calculation can be applied to any restriction enzyme as long as the length of its recognition site is known, making it possible to predict the size and number of a DNA fragments that would be obtained by cutting a DNA molecule of known size. This allows one of skill in the art to produce DNA fragments of known size. Restriction endonucleases are obtained from bacteria or are produced through recombinant technology and are readily available through numerous commercial sources.

In the restriction endonuclease fragmentation method, a restriction endonuclease is combined with a sample of genomic DNA and buffer appropriate for optimal activity of the endonuclease. In general, 1 unit of endonuclease will digest 1 µg of DNA in 1 hour at 37° C.

One of skill in the art would recognize that this fragmentation method can be modified by using a restriction enzyme that cuts at a particular frequency or a particular site, or by using multiple restriction enzymes. The choice of enzyme or enzyme combinations is chosen to suit the gene of interest in an assay. In general, one would choose an enzyme or enzyme combination to generate a fragment containing the entire tandem repeat region and the upstream or downstream marker sequence. Enzymes for fragmentation can be chosen by using a restriction enzyme map of the region surrounding the tandem repeat. Such maps can be readily generated by software programs well-known to those of skill in the art.

In particular, one would choose an enzyme or a combination of enzymes to obtain an appropriately sized fragment to distinguish a normal length tandem repeat region from an abnormal length tandem repeat region. In determining an appropriate size for a fragment, one would consider the difference in the range of lengths of a normal tandem repeat region as compared to that for an abnormal tandem repeat region. For example, if the difference between a normal tandem repeat region and an abnormal tandem repeat region is small, one would choose a shorter length fragment, whereas if the difference is large one would choose a longer length fragment.

In preferred embodiments, AluI is used to fragment the nucleic acids. AluI is a restriction enzyme that recognizes a 4-nucleotide sequence of double-stranded DNA (i.e., —AGCT—). One of skill in the art would recognize that isoschizomers (i.e., restriction enzymes with the same recognition sequence and cut site) of AluI can be readily substituted for AluI. Examples of AluI isoschizomers include, but are not limited to, BsaLI, MarI, MltI, and OxaI One of skill in the art would further recognize that a neoschizomer (i.e., a restriction enzyme with the same recognition sequence as another enzyme but with a different cut site) of AluI could also be substituted for AluI.

One of skill in the art would recognize that other restriction enzymes with the same cutting frequency as AluI could be substituted for AluI in this method. For example, AluI, which recognizes a 4-nucleotide sequence, cuts DNA at approximately every 256 bases. Other enzymes with different 4-nucleotide recognition sequences (e.g., DpnI, RsaI, MboI, and NlaI) would be expected to cut at a similar frequency to AluI and would therefore produce fragments of a size similar to those of AluI.

In other preferred embodiments, BlpI and MlyI are used in combination to fragment the nucleic acids. In still other preferred embodiments, SphI and BmtI are used in combination to fragment the nucleic acids.

Size Separation of DNA Fragments

Separation of DNA fragments according to size may be accomplished by various methods known to those of skill in the art. For example, various methods of gel electrophoresis or column chromatography (e.g., size-exclusion high performance liquid chromatography (SEC-HPLC) and denaturing HPLC (DHPLC)) may be used.

In gel electrophoresis, a gel matrix, to which an electric field is applied, is utilized to separate nucleic acid molecules or fragments thereof based on size. In general, smaller nucleic acid fragments will move faster through the gel matrix than larger fragments. Preferred gel matrices include agarose and polyacrylamide.

In preferred embodiments, capillary electrophoresis is used to separate the fragmented nucleic acids. Capillary electrophoresis is a separation method based on the differential electrophoretic migration rate of sample components in a capillary when a voltage is applied. Separated fragments or molecules are generally detected "on-column" using UV spectrometric or fluorescence analysis through a window in the capillary. In general, one or more standards (i.e., a segment of nucleic acid having known length) are first injected into the capillary to determine the elution time for each standard using on-column detection. Then, the elution times of the standards are used to determine the length of time over which a fraction will be collected in order to achieve a desired size range for that fraction.

In some embodiments, the size ranges for the fractions used in an assay may be chosen based on the length in base pairs of commercially-available standards. A number of standards are available containing mixtures of lengths of nucleic acids. In one example, a standard containing nucleic acid fragments having the following lengths is used: 200 bp, 300 bp, 400 bp, 500 bp, 600 bp, 700 bp, 800 bp, 900 bp, and 1000 bp. Thus, fractions would then be chosen based on one or more of the sizes present in the standard. For example, one might choose the following three fractions: 1) less than or equal to 300 bp, 2) 301-500 bp, and 3) greater than or equal to 501. One would then collect fractions of the fragmented nucleic acid sample based on the elution times of the 300 bp and 500 bp standards. The range in number of tandem repeats present in each fraction can be calculated.

Alternatively, fractions can be chosen based on a desired number of tandem repeats for each fraction. In this case, standards representing the upper and lower limits in size of each fraction can be synthesized if not commercially available.

In some embodiments, the fragments are separated into the lowest number of fractions in order to distinguish normal from abnormal length tandem repeat regions. In particular embodiments, the fragments may be separated into two fractions, one corresponding to a normal tandem repeat region and one corresponding to an abnormal tandem repeat region.

In other embodiments, the fragments are separated into a larger number of fractions in order to determine the size of the tandem repeat region. In general, more fractions will allow a more precise determination of the length of the tandem repeat region. The number of fractions may be chosen in order to achieve a desired level of precision in determining the length of the tandem repeat region.

In a preferred embodiment of the assay to determine the number of tandem repeats of the FMR1 gene, AluI fragmented DNA is separated into two fractions corresponding to sizes of approximately 211-358 bp (lower fraction) and 359 bp-9 kb (upper fraction). Fragments from samples containing a normal FMR1 gene (i.e., less than 55 tandem repeats), will separate into the lower fraction, whereas fragments from FMR1 genes containing premutations (i.e., 55-200 tandem repeats) or full mutations (i.e., greater than 200 tandem repeats) will separate into the upper fraction.

In another preferred embodiment of the assay to determine the number of tandem repeats of the FMR1 gene, AluI fragmented DNA is separated into two fractions corresponding to sizes of approximately 211-400 bp (lower fraction) and 401 bp-9 kb (upper fraction). Fragments from samples containing a normal FMR1 gene (i.e., less than 55 tandem repeats) and permutations having 56-69 tandem repeats, will separate into the lower fraction, whereas fragments from FMR1 genes containing premutations having 70-200 tandem repeats or full mutations (i.e., greater than 200 tandem repeats) will separate into the upper fraction.

In another preferred embodiment of the assay to determine the number of tandem repeats of the FMR1 gene, AluI fragmented DNA is separated into four fractions corresponding to sizes of approximately less than or equal to 400 bp (first/lowest fraction), 401-500 bp (second fraction), 501-800 bp (third fraction) and 800 bp-9 kb (fourth/highest fraction). Fragments from samples containing a normal FMR1 gene (i.e., less than 55 tandem repeats) and those containing permutations having 56-68 tandem repeats will separate into the first/lowest fraction, whereas fragments from FMR1 genes containing small premutations (i.e., 69-102 tandem repeats) will separate into the second fraction, whereas fragments from FMR1 genes containing large permutations (i.e., 103-200 tandem repeats) and full mutations having 201-202 tandem repeats will separate into the third fraction, and whereas full mutations having greater than 202 tandem repeats will separate into the fourth/highest fraction.

In yet another preferred embodiment of the assay to determine the number of tandem repeats of the FMR1 gene, DNA fragmented with a combination of SphI and BmtI is separated into four fractions corresponding to sizes of approximately less than or equal to 500 bp (first/lowest fraction), 501-800 bp (second fraction), 801-900 bp (third fraction) and 901 bp-9 kb (fourth/highest fraction). Fragments from samples containing a normal FMR1 gene (i.e., less than 55 tandem repeats) and those containing permutations having 56-62 tandem repeats will separate into the first/lowest fraction, whereas fragments from FMR1 genes containing small premutations (i.e., 63-163 tandem repeats) will separate into the second fraction, whereas fragments from FMR1 genes containing large permutations (i.e., 164-196 tandem repeats) will separate into the third fraction, and whereas large premutations having 197-200 tandem repeats and full mutations (i.e., greater than 200 tandem repeats) will separate into the fourth/highest fraction.

In still another preferred embodiment of the assay to determine the number of tandem repeats of the FMR1 gene, DNA fragmented with a combination of BlpI an dMlyI is separated into four fractions corresponding to sizes of approximately less than or equal to 603 bp (first/lowest fraction), 604-840 bp (second fraction), 841-1078 bp (third fraction) and 1079 bp-9 kb (fourth/highest fraction). Fragments from samples containing a normal FMR1 gene (i.e., less than 55 tandem repeats) and those containing permutations having 56-62 tandem repeats will separate into the first/lowest fraction, whereas fragments from FMR1 genes containing small premutations (i.e., 63-140 tandem repeats) will separate into the second fraction, whereas fragments from FMR1 genes containing large permutations (i.e., 141-200 tandem repeats) and full mutations having 201-220 tandem repeats will separate into the third fraction, and whereas large premutations having greater than 220 tandem repeats will separate into the fourth/highest fraction.

In another preferred embodiment, fragmented DNA is separated into a multiplicity of fractions, according to size. Automated fraction collection is accomplished using, for example, a preset fraction time window, beginning at approximately 200 bp and ending at 9 kb. This method allows for a finer estimation of fragment size and thereby, an estimation of the number of repeats.

Second Fragmentation of DNA

In yet other preferred embodiments, the methods of the invention include a second nucleic acid fragmentation following the size separation of the first nucleic acid fragmentation. Preferably, a restriction endonuclease digestion is used to further fragment the DNA. Preferably, the second fragmentation separates the tandem repeat segment from an associated marker sequence.

In preferred embodiments, restriction enzyme BsaWI, Hpy188I, HphI or BstNI is used for the second nucleic acid fragmentation when the marker sequence is upstream of the tandem repeat segment. In other preferred embodiments, restriction enzyme SmlI, BbvI, or BmtI is used for the second nucleic acid fragmentation when the marker sequence is downstream of the tandem repeat segment One of skill in the art would recognize that isoschizomers and neoschizomers of the listed restriction enzymes could also be used. One of skill in the art would be able to identify a suitable restriction enzyme for the second nucleic acid fragmentation by analyzing factors which include, but are not limited to, the location of the marker, the sequence of the marker and the sequence between the marker sequence and the tandem repeat segment.

Amplification of Size-Separated DNA Fragments or DNA Fragments Following Second Fragmentation Size-separated DNA may be amplified by various methods known to the skilled artisan. Amplification methods suitable for use with the present methods include, for example, polymerase chain reaction (PCR), ligase chain reaction (LCR), transcription-based amplification system (TAS), nucleic acid sequence based amplification (NASBA) reaction, self-sustained sequence replication (3SR), strand displacement amplification (SDA) reaction, boomerang DNA amplification (BDA), Q-beta replication, or isothermal nucleic acid sequence based amplification. These methods of amplification each described briefly below and are well-known in the art.

PCR is a technique for making many copies of a specific template DNA sequence. The reaction consists of multiple amplification cycles and is initiated using a pair of primer sequences that hybridize to the 5' and 3' ends of the sequence to be copied. The amplification cycle includes an initial denaturation, and up to 50 cycles of annealing, strand elongation and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, *Journal of Clinical Microbiology*, 33(3):556-561(1995). Briefly, a PCR reaction mixture includes two specific primers, dNTPs, approximately 0.25 U of Taq polymerase, and 1×PCR Buffer. For every 25 µl PCR reaction, 2 µl sample (e.g., isolated DNA from target organism) is added and amplified using a thermal cycler.

LCR is a method of DNA amplification similar to PCR, except that it uses four primers instead of two and uses the enzyme ligase to ligate or join two segments of DNA. LCR can be performed as according to Moore et al., *Journal of Clinical Microbiology* 36(4):1028-1031 (1998). Briefly, an LCR reaction mixture contains two pair of primers, dNTP, DNA ligase and DNA polymerase representing about 90 µl, to which is added 100 µl of isolated nucleic acid from the target organism. Amplification is performed in a thermal cycler (e.g., LCx of Abbott Labs, North Chicago, Ill.).

TAS is a system of nucleic acid amplification in which each cycle is comprised of a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS* 86:1173-7 (1989). Briefly, extracted RNA is combined with TAS amplification buffer and bovine serum albumin, dNTPs, NTPs, and two oligonucleotide primers, one of which contains a PBS. The sample is heated to denature the RNA template and cooled to the primer annealing temperature. Reverse transcriptase (RT) is added the sample incubated at the appropriate temperature to allow cDNA elongation. Subsequently T7 RNA polymerase is added and the sample is incubated at 37° C. for approximately 25 minutes for the synthesis of RNA. The above steps are then repeated. Alternatively, after the initial cDNA synthesis, both RT and RNA polymerase are added following a 1 minute 100° C. denaturation followed by an RNA elongation of approximately 30 minutes at 37° C. TAS can be also be performed on solid phase as according to Wylie et al., *Journal of Clinical Microbiology*, 36(12):3488-3491 (1998). In this method, nucleic acid targets are captured with magnetic beads containing specific capture primers. The beads with captured targets are washed and pelleted before adding amplification reagents which contains amplification primers, dNTP, NTP, 2500 U of reverse transcriptase and 2500 U of T7 RNA polymerase. A 100 µl TMA reaction mixture is placed in a tube, 200 µl oil reagent is added and amplification is accomplished by incubation at 42° C. in a waterbath for one hour.

NASBA is a transcription-based amplification method which amplifies RNA from either an RNA or DNA target. NASBA is a method used for the continuous amplification of nucleic acids in a single mixture at one temperature. For example, for RNA amplification, avian myeloblastosis virus (AMV) reverse transcriptase, RNase H and T7 RNA polymerase are used. This method can be performed as according to Heim, et al., *Nucleic Acids Res.*, 26(9):2250-2251 (1998). Briefly, an NASBA reaction mixture contains two specific primers, dNTP, NTP, 6.4 U of AMV reverse transcriptase, 0.08 U of *Escherichia coli* Rnase H, and 32 U of T7 RNA polymerase. The amplification is carried out for 120 min at 41° C. in a total volume of 20 µl.

In a related method, self-sustained sequence-replication (3SR) reaction, isothermal amplification of target DNA or RNA sequences in vitro using three enzymatic activities: reverse transcriptase, DNA-dependent RNA polymerase and *Escherichia coli* ribonuclease H. This method may be modified from a 3-enzyme system to a 2-enzyme system by using human immunodeficiency virus (HIV)-1 reverse transcriptase instead of avian myeloblastosis virus (AMV) reverse transcriptase to allow amplification with T7 RNA polymerase but without *E. coli* ribonuclease H. In the 2-enzyme 3SR, the amplified RNA is obtained in a purer form compared with the 3-enzyme 3SR (Gebinoga & Oehlenschlager *European Journal of Biochemistry*, 235:256-261, 1996).

SDA is an isothermal nucleic acid amplification method. A primer containing a restriction site is annealed to the template. Amplification primers are then annealed to 5' adjacent sequences (forming a nick) and amplification is started at a fixed temperature. Newly synthesized DNA strands are nicked by a restriction enzyme and the polymerase amplification begins again, displacing the newly synthesized strands. SDA can be performed as according to Walker, et al., *PNAS*, 89:392-6 (1992). Briefly, an SDA reaction mixture contains four SDA primers, dGTP, dCTP, TTP, dATP, 150 U of Hinc II, and 5 U of exonuclease-deficient of the large fragment of *E. coli* DNA polymerase I (exo⁻ Klenow polymerase). The sample mixture is heated 95° C. for 4 minutes to denature target DNA prior to addition of the enzymes. After addition of the two enzymes, amplification is carried out for 120 min. at 37° C. in a total volume of 50 µl. Then, the reaction is terminated by heating for 2 minutes at 95° C.

Boomerang DNA amplification (BDA) is a method in which the polymerase begins extension from a single primer-binding site and then makes a loop around to the other strand, eventually returning to the original priming site on the DNA. BDA is differs from PCR through its use of a single primer. This method involves an endonuclease digestion of a sample DNA, producing discrete DNA fragments with sticky ends, ligating the fragments to "adapter" polynucleotides (comprised of a ligatable end and first and second self-complementary sequences separated by a spacer sequence) thereby forming ligated duplexes. The ligated duplexes are denatured to form templates to which an oligonucleotide primer anneals at a specific sequence within the target or marker sequence of interest. The primer is extended with a DNA polymerase to form duplex products followed by denaturation of the duplex products. Subsequent multiple cycles of annealing, extending, and denaturing are performed to achieve the desired degree of amplification (U.S. Pat. No. 5,470,724).

The Q-beta replication system uses RNA as a template. Q-beta replicase synthesizes the single-stranded RNA genome of the coliphage Qβ. Cleaving the RNA and ligating in a nucleic acid of interest allows the replication of that sequence when the RNA is replicated by Q-beta replicase (Kramer & Lizardi *Trends Biotechnol.* 1991 9(2):53-8, 1991).

A variety of amplification enzymes are well known in the art and include, for example, DNA polymerase, RNA polymerase, reverse transcriptase, Q-beta replicase, thermostable DNA and RNA polymerases. Because these and other amplification reactions are catalyzed by enzymes, in a single step assay the nucleic acid releasing reagents and the detection reagents should not be potential inhibitors of amplification enzymes if the ultimate detection is to be amplification based. Amplification methods suitable for use with the present methods include, for example, strand displacement amplification, rolling circle amplification, primer extension preamplification, or degenerate oligonucleotide PCR (DOP). These methods of amplification are well known in the art and each described briefly below.

Preferably, PCR is used to amplify a target or marker sequence flanking the tandem repeat segment of interest. In this method, two or more oligonucleotide primers that anneal to opposite strands of a target or marker sequence are repetitively annealed to their complementary sequences, extended by a DNA polymerase (e.g., AmpliTaq Gold polymerase), and heat denatured, resulting in exponential amplification of the target nucleic acid sequences. Cycling parameters can be varied, depending on the length of nucleic acids to be extended. The skilled artisan is capable of designing and preparing primers that are appropriate for amplifying a target or marker sequence. The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well-known to a person of ordinary skill and include considerations described herein. For example, the length of a short nucleic acid or oligonucleotide can relate to its hybridization specificity or selectivity.

In some embodiments, the amplification may include a labeled primer, thereby allowing detection of the amplification product of that primer. In particular embodiments the amplification may include a multiplicity of labeled primers, preferably such primers are distinguishably labeled, allowing the simultaneous detection of multiple amplification products.

Oligonucleotide primers can be designed which are between about 10 and about 100 nucleotides in length and hybridize to the marker sequence. Oligonucleotide primers are preferably 12 to 70 nucleotides; more preferably 15-60 nucleotides in length; and most preferably 15-25 nucleotides in length.

In one embodiment, a primer pair is designed to amplify a marker sequence upstream of the tandem repeat region of the FMR1 gene following size separation of nucleic acids fragmented by AluI. An exemplary marker sequence upstream of the FMR1 tandem repeat region for designing hybridization primers is depicted in FIG. 2 (SEQ ID NO:1). A forward primer can hybridize to SEQ ID NO:1 between nucleotides 1 and 45, more preferably between positions 22 and 39 while a reverse primer can hybridize to SEQ ID NO:1 between positions 70 and 115, more preferably between 97 and 113. One example is to use a primer pair to amplify a region of the flanking sequence corresponding to approximately 95 bp upstream of the tandem repeat region; more specifically using a forward primer, SEQ ID NO:4 and a reverse primer, SEQ ID NO:5 to amplify a 93 bp region of the marker sequence. Thus, preferred oligonucleotides which may be used as amplification primers include SEQ ID NO:4 (5'-GGTGGAGGGC-CGCCTCTG-3') and SEQ ID NO:5 (5'-AGCGGCGCCTC-CGTCACC-3'). Other preferred oligonucleotide primers are approximately 15-100 nucleotides in length and comprise SEQ ID NO:4 or SEQ ID NO:5. Still other preferred oligonucleotide primers include an oligonucleotide sequence that hybridizes to the complement of a 15-100 nucleotide sequence including SEQ ID NO:4 or SEQ ID NO:5. Such oligonucleotides may be substantially purified.

TABLE 2

Primers for amplifying marker sequences flanking FMR1

| Primer Name | SEQ ID NO: | Primer Sequence |
| --- | --- | --- |
| FMR1F4 | 4 | 5'-GGTGGAGGGCCGCCTCTG-3' |
| FMR1R4 | 5 | 5'-AGCGGCGCCTCCGTCACC-3' |
| FXCEF2 | 6 | 5'-GATGGAGGAGCTGGTGGTGG-3' |
| FXCER2 | 7 | 5'-GGAAGGGCGAAGATGGGG-3' |
| FXCEF3 | 8 | 5'-CGTGACGTGGTTTCAGTGTTTACA-3' |
| FXCER3 | 9 | 5'GGAAGTGAAACCGAAACGGAG-3' |

In another embodiment, a primer pair is designed to amplify a marker sequence flanking the tandem repeat region of the FMR1 gene following size separation of nucleic acids fragmented by BlpI and MlyI. In one example, a primer pair is used to amplify a region of the flanking sequence downstream of the tandem repeat region; more specifically using a forward primer, FXCEF2 (SEQ ID NO:6), and a reverse primer, FXCER2 (SEQ ID NO:7), to amplify an 86 bp region of the marker sequence. Thus, preferred oligonucleotides which may be used as amplification primers include SEQ ID NO:6 (5'-GATGGAGGAGCTGGTGGTGG-3') and SEQ ID NO:7 (5'-GGAAGGGCGAAGATGGGG-3'). Other preferred oligonucleotide primers are approximately 15-100 nucleotides in length and comprise SEQ ID NO:6 or SEQ ID NO:7. Still other preferred oligonucleotide primers include an oligonucleotide sequence that hybridizes to the complement of a 15-100 nucleotide sequence including SEQ ID NO:6 or SEQ ID NO:7. Such oligonucleotides may be substantially purified.

In another embodiment, a primer pair is designed to amplify a marker sequence flanking the tandem repeat region of the FMR1 gene following size separation of nucleic acids fragmented by SphI and BmtI. In one example, a primer pair is used to amplify a region of the flanking sequence downstream of the tandem repeat region; more specifically using a forward primer, FXCEF3 (SEQ ID NO:8), and a reverse primer, FXCER3 (SEQ ID NO:9), to amplify an 86 bp region of the marker sequence. Thus, preferred oligonucleotides which may be used as amplification primers include SEQ ID NO:8 (5'-CGTGACGTGGTTTCAGTGTTTACA-3') and SEQ ID NO:9 (5'-GGAAGTGAAACCGAAACGGAG-3'). Other preferred oligonucleotide primers are approximately 15-100 nucleotides in length and comprise SEQ ID NO:8 or SEQ ID NO:9. Still other preferred oligonucleotide primers include an oligonucleotide sequence that hybridizes to the complement of a 15-100 nucleotide sequence including SEQ ID NO:8 or SEQ ID NO:9. Such oligonucleotides may be substantially purified.

Assay controls may be used in the assay for detecting carriers and individuals afflicted with fragile X syndrome. Positive controls for normal or wild type FMR1 gene (i.e., less than 55 tandem repeats), the premutation (55-200 tandem repeats), and the full mutation (greater than 200 tandem repeats) may be used.

Additional controls may be included in the assay to determine if the restriction enzyme digestion of the genomic DNA is complete. One approach to evaluate the completeness of digestion by a particular restriction enzyme is to determine if the digested DNA can support a PCR amplification using a test primer pair that spans the restriction enzyme site used for digestion. Thus, if the nucleic acid has been fully digested by the restriction enzyme, there should be no amplification from the test primer pair, however, if digestion is incomplete, leaving some intact nucleic acid, the test primer pair should amplify the target. This test digestion PCR amplification can be conducted anytime after digestion including during amplification of the marker sequence.

TABLE 3

Exemplary control primers

| Primer Name | SEQ ID NO: | Primer Sequence |
|---|---|---|
| AluIF | 10 | 5'-CTCCAATGCCTCCTGCGTCC-3' |
| AluIR | 11 | 5'-GGGGGTAGGGAGTGTCTGAGAGTCT-3' |
| BlpIF | 12 | 5'-AGTGTTTAGAAGGAAAAGGCTGAGC-3' |

TABLE 3-continued

Exemplary control primers

| Primer Name | SEQ ID NO: | Primer Sequence |
|---|---|---|
| BlpIR | 13 | 5'-GCCCAAAGTTTCATAGGTAGCAAA-3' |
| LargeF | 14 | 5'-CACCCTACAAGCCGTCGCTAACA-3' |
| LargeR | 15 | 5'-CGTGCCTTGTCGGTATCATTAGCAA-3' |
| FIIctrl1F | 16 | 5'-CTGAATTTGTTTGGTTTGATGATGC-3' |
| FIIctrl1R | 17 | 5'-CCTGTGTTATCTGTGCCCATTTTAA-3' |
| FIIIctrl3F | 18 | 5'-/6-FAM/ATCTGGGTCTGAATAATGTGAGGAG-3' |
| FIIIctrl3R | 19 | 5'-CCTAACTTTCATTCTTGTCACCCTT-3' |
| LgctrIF | 20 | 5'-/6-FAM/AGGTTTGAGTGTATCGCCTGATAGA-3' |
| LgctrIR | 21 | 5'-TGAGTTTCATGTTTGCTCTTGCTC-3' |
| AluIFtaq | 22 | 5'-GCCTCCTGCGTCCTTGTAGA-3' |
| AluIRtaq | 23 | 5'-TGAGAGTCTTGTTTCAGCAGTGTTAA-3' |
| LargeFtaq | 24 | 5'-CAAGCCGTCGCTAACAAGGA-3' |
| LargeRtaq | 25 | 5'-GATGTCTTGTATGGTGCCCTCAT-3' |

In a particular embodiment of an assay to distinguish normal individuals from carriers and affected individuals of fragile X syndrome, the genomic DNA is digested with AluI. Thus, the completion of the digestion of genomic DNA by AluI can be determined by amplifying a region containing an AluI recognition site. In one example of such a control, a pair of primers, AluIF and AluIR (SEQ ID NO:10 and SEQ ID NO:11, respectively) are used to amplify a 103 bp target segment of a nucleic acid fragment containing an AluI recognition site. Amplification of this segment will only occur when AluI digestion is incomplete. In another embodiment of this assay, the genomic DNA is digested with BlpI and MlyI. Thus, the completion of the digestion of genomic DNA by BlpI and MlyI can be determined by amplifying a region containing a BlpI or an MlyI recognition site. In one example of such a control, a pair of primers, BlpIF and BlpIR (SEQ ID NO:12 and SEQ ID NO:13, respectively) are used to amplify a 138 bp segment of target segment of nucleic acid containing a BlpI recognition site. Amplification of this segment will only occur when BlpI digestion is incomplete.

Additional controls may be included in the assay to verify proper size-separation of fragmented DNA. Using sequence analysis tools known to those of skill in the art, one could determine the size distribution of fragments obtained using a particular restriction enzyme. One could then identify a specific control fragment having a size that corresponds to the size range of a particular fraction. Thus one could verify proper size separation of the fragmented DNA by detecting the control fragment in the appropriate fraction for its size. One could use a single control fragment in one fraction, a control in each fraction relevant to the determination of a normal versus abnormal tandem repeat, or a control fraction in all fractions.

In a particular embodiment of an assay to distinguish normal individuals from carriers and affected individuals of fragile X syndrome, a control amplification is also included to determine if the largest tandem repeat-containing fragments (obtained through digestion with AluI) are collected into the size-appropriate fraction. In one example of such a control, a pair of primers, LargeF and LargeR (SEQ ID NO:14 and SEQ ID NO:15, respectively) will amplify a 121 bp segment of an 8,479 bp AluI fragment of the USP41 gene when present in a fraction. In another embodiment of the assay, in which the genomic DNA is digested with BlpI and MlyI, controls are included to detect proper size separation of fragments of 675 bp, 905 bp, and 7,031 bp. In one example, a pair of primers, FIIctrl1F and FIIctrl1R (SEQ ID NO:16 and SEQ ID NO:17, respectively) will amplify a 102 bp segment of a 675 bp BlpI/MlyI fragment of the CFTR gene when present in a fraction. In another example, a pair of primers, FIIctrl3F and FIIctrl3R (SEQ ID NO:18 and SEQ ID NO:19, respectively) will amplify a 113 bp segment of a 905 bp BlpI/MlyI fragment of the CFTR gene when present in a fraction. In another example, a pair of primers, LgctrlF and LgctrlR (SEQ ID NO:20 and SEQ ID NO:21, respectively) will amplify a 156 bp segment of a 7,031 bp BlpI/MlyI fragment from chromosome 21 (21:20912766-20919795) when present in a fraction.

Detection of Marker Sequences

Marker sequences may be amplified prior to detection or may be detected directly after size separation without an amplification step. In some embodiments, the marker sequence is amplified and the resulting amplicon is detected by electrophoresis, preferably capillary electrophoresis. In preferred embodiments, the marker sequence is amplified using a labeled primer such that the resulting amplicon is detectably labeled. In preferred embodiments, the primer is fluorescently labeled, however, the primers may be labeled according to the methods described below for oligonucleotide probes.

In preferred embodiments, the fragmented DNA is detected directly, without an amplification step, using two distinguishably-labeled nucleic acid probes which hybridize to two separate segments of a marker sequence upstream or downstream of the tandem repeats. The simultaneous detection of both labels in one hybridization complex indicates the presence of the marker sequence (and thus the associated tandem repeat). In one embodiment, detection is accomplished using a Trilogy 2020 Analyzer (US Genomics Woburn, Mass.). In this embodiment, two probes with distinguishable fluorescent labels are contacted with the size-separated DNA fragments. The resulting mixture of hybridization complexes is directed into a capillary tube where it is exposed to multiple lasers of differing wavelengths. The fluorescent labels of the probes are excited such that photons are emitted and detected. The simultaneous detection of fluorescent labels of different colors indicates the presence of the target region.

Probe oligonucleotides may be detectably labeled by methods known in the art. Useful labels include, e.g., fluorescent dyes (e.g., Cy5®, Cy3®, FITC, rhodamine, lanthamide phosphors, Texas Red®), $^{32}$P, $^{35}$S, $^{3}$H, $^{14}$C, $^{125}$I, $^{131}$I, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, digoxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) or antibody that hybridizes or binds to the nucleic acid to be detected.

In preferred embodiment the detectable label is a fluorophore. The term "fluorophore" as used herein refers to a molecule that absorbs light at a particular wavelength (excitation frequency), and subsequently emits light of a different, typically longer, wavelength (emission frequency) in response. Suitable fluorescent moieties include the following fluorophores known in the art:
4-acetamido-4'-isothiocyanatostilbene-2,2' disulfonic acid
acridine and derivatives:
   acridine
   acridine isothiocyanate
Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes)
5-(2'-aminoethyl)aminonaphthalene-1-sulfonic acid (EDANS)
4-amino-N-[3-vinylsulfonyl)phenyl]naphthalimide-3,5 disulfonate (Lucifer Yellow VS)
N-(4-anilino-1-naphthyl)maleimide
anthranilamide
Black Hole Quencher™ (BHQ™) dyes (biosearch Technologies)
BODIPY® R-6G, BOPIPY® 530/550, BODIPY® FL
Brilliant Yellow
coumarin and derivatives:
   coumarin
   7-amino-4-methylcoumarin (AMC, Coumarin 120)
7-amino-4-trifluoromethylcouluarin (Coumarin 151)
Cy2 Cy3'Cy3.5 Cy5®, Cy5.5®
cyanosine
4',6-diaminidino-2-phenylindole (DAPI)
5',5"-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
Eclipse™ (Epoch Biosciences Inc.)
eosin and derivatives:
   eosin
   eosin isothiocyanate
erythrosin and derivatives:
   erythrosin B
   erythrosin isothiocyanate
ethidium
fluorescein and derivatives:
   5-carboxyfluorescein (FAM)
   5-(4,6-dichlorotriazin-2-yl)aminofluorescein (DTAF)
   2',7'-dimethoxy-4'5'-dichloro-6-carboxyfluorescein (JOE)
   fluorescein
   fluorescein isothiocyanate (FITC)
   hexachloro-6-carboxyfluorescein (HEX)
   QFITC (XRITC)
   tetrachlorofluorescein (TET)
fluorescamine
IR144
IR1446
Malachite Green isothiocyanate
4-methylumbelliferone ortho cresolphthalein
nitrotyrosine
pararosaniline
Phenol Red
B-phycoerythrin, R-phycoerythrin
o-phthaldialdehycle
Oregon Green®
propidium iodide
pyrene and derivatives:
   pyrene
   pyrene butyrate
   succinimidyl 1-pyrene butyrate
QSY® 7, QSY® 9, QSY® 21, QSY® 35 (Molecular Probes)
Reactive Red 4 (CibacronC Brilliant Red 3B-A)
rhodamine and derivatives:
   6-carboxy-X-rhodamine (ROX)
   6-carboxyrhodamine (R6G)
   lissaminc rhodamine B sulfonyl chloride
   rhodamine (Rhod)
   rhodamine B
   rhodamine 123
   rhodamine green
   rhodamine X isothiocyanate
   sulforhodamine B
   sulforhodamine 101
   sulfonyl chloride derivative of sulforhodamine 101 (Texas Red®)
N,N,N',N'-tetramethyl-6-carboxyrhodamine (TAMRA)
tetramethyl rhodamine
tetramethyl rhodamine isothiocyanate (TRITC)
riboflavin
rosolic acid
terbium chelate derivatives Other fluorescent nucleotide analogs can be used, see, e.g., Jameson, Meth. Enzymol. 278:363-390, 1997; Zhu, Nucl. Acids Res. 22:3418-3422, 1994. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, Mol. Cell. Probes 9:145-156, 1995.

Detectable labels can be incorporated into nucleic acids by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., Cy3® or Cy5® and then incorporated into genomic nucleic acids during nucleic acid synthesis or amplification. Nucleic acids can thereby be labeled when synthesized using Cy3®- or Cy5®-dCTP conjugates mixed with unlabeled dCTP.

Nucleic acid probes can be labeled by using PCR or nick translation in the presence of labeled precursor nucleotides, for example, modified nucleotides synthesized by coupling allylamine-dUTP to the succinimidyl-ester derivatives of the fluorescent dyes or haptens (such as biotin or digoxigenin) can be used; this method allows custom preparation of most common fluorescent nucleotides, see, e.g., Henegariu, Nat. Biotechnol. 18:345-348, 2000.

Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulphur containing side chains of amino acids. See, e.g., U.S. Pat. Nos. 5,580,990; 5,714,327; and 5,985,566; and European Patent No. 0539466.

The binding of a probe to the marker sequence flanking the tandem repeat region may be determined by hybridization as is well known in the art. Hybridization may be detected in real time or in non-real time.

One general method for real time PCR uses fluorescent probes such as the TaqMan® probes, molecular beacons and scorpions. The probes employed in TaqMan® and molecular beacon technologies are based on the principle of fluorescence quenching and involve a donor fluorophore and a quenching moiety.

The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and either dissipates the energy as heat or emits light of a longer wavelength than the emission wavelength of the donor. In the latter case, the quencher is considered to be an acceptor fluorophore. The quenching moiety can act via proximal (i.e. collisional) quenching or by Förster or fluorescence resonance energy transfer ("FRET"). Quenching by FRET is generally used in TaqMan® probes while proximal quenching is used in molecular beacon and scorpion type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on $R^{-6}$, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from increased distance between the donor and the quencher (acceptor fluorophore).

TaqMan® probes (Heid et al., 1996) use the fluorogenic 5' exonuclease activity of Taq polymerase to measure the amount of target or marker sequences in DNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo)benzoic acid (DABCYL). See Tyagi et al., Nature Biotechnology 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase replicates a template on which a TaqMan® probe is bound, its 5' exonuclease activity cleaves the probe. This ends the activity of quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

TaqMan® assay uses universal thermal cycling parameters and PCR reaction conditions. Because the cleavage occurs only if the probe hybridizes to the target, the fluorescence detected originates from specific amplification. The process of hybridization and cleavage does not interfere with the exponential accumulation of the product. One specific requirement for fluorogenic probes is that there be no G at the 5' end. A 'G' adjacent to the reporter dye quenches reporter fluorescence even after cleavage.

Other methods of probe hybridization detected in real time can be used for detecting amplification a target or marker sequence flanking a tandem repeat region. For example, the commercially available MGB Eclipse™ probes (Epoch Biosciences), which do not rely on a probe degradation can be used. MGB Eclipse™ probes work by a hybridization-triggered fluorescence mechanism. MGB Eclipse™ probes have the Eclipse™ Dark Quencher and the MGB positioned at the 5'-end of the probe. The fluorophore is located on the 3'-end of the probe. When the probe is in solution and not hybridized, the three dimensional conformation brings the quencher into close proximity of the fluorophore, and the fluorescence is quenched. However, when the probe anneals to a target or marker sequence, the probe is unfolded, the quencher is moved from the fluorophore, and the resultant fluorescence can be detected.

Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like. Suitable quenchers include tetra-methylcarboxyrhodamine (TAMRA) 4-(4-dimethylaminophenylazo)benzoic acid ("DABCYL" or a DABCYL analog) and the like. Tetramethylrhodamine (TMR) or 5-carboxyrhodamine 6G (RHD) may be combined as donor fluorophores with DABCYL as quencher. Multiplex TaqMan® assays can be performed using multiple detectable labels each comprising a different donor and quencher combination. Probes for detecting amplified sequence in real time may be stored frozen (−10° to −30° C.) as 100 µM stocks. TaqMan® probes are available from Applied BioSystems (4316032).

In a preferred embodiment, real time PCR is performed using TaqMan® probes in combination with a suitable amplification/analyzer such as the ABI Prism 7900HT Sequence Detection System. The ABI PRISM® 7900HT Sequence Detection System is a high-throughput real-time PCR system that detects and quantitates nucleic acid sequences. Briefly, TaqMan™ probes specific for the amplified target or marker sequence are included in the PCR amplification reaction. These probes contain a reporter dye at the 5' end and a quencher dye at the 3' end. Probes hybridizing to different target or marker sequences are conjugated with a different fluorescent reporter dye. During PCR, the fluorescently labeled probes bind specifically to their respective target or marker sequences; the 5' nuclease activity of Taq polymerase cleaves the reporter dye from the probe and a fluorescent signal is generated. The increase in fluorescence signal is detected only if the target or marker sequence is complementary to the probe and is amplified during PCR. A mismatch between probe and target greatly reduces the efficiency of probe hybridization and cleavage. The ABI Prism 7700HT or 7900HT Sequence detection System measures the increase in fluorescence during PCR thermal cycling, providing "real time" detection of PCR product accumulation.

Real Time detection on the ABI Prism 7900HT or 7900HT Sequence Detector monitors fluorescence and calculates Rn during each PCR cycle. The threshold cycle, or Ct value, is the cycle at which fluorescence intersects the threshold value. The threshold value is determined by the sequence detection system software or manually.

Oligonucleotide probes can be designed which are between about 10 and about 100 nucleotides in length and hybridize to the amplified region. Oligonucleotides probes are preferably 12 to 70 nucleotides; more preferably 15-60 nucleotides in length; and most preferably 15-25 nucleotides in length. The probe may be labeled. In one example, SEQ ID NO:26 can be used as an oligonucleotide probe to detect a marker sequence associated with the tandem repeat region of the FMR1 gene (following genomic fragmentation by AluI), when the marker sequence is amplified by forward and reverse primers as set forth in SEQ ID NO:4 and SEQ ID NO:5, respectively. SEQ ID NO:27 can be used to detect an AluI control fragment amplicons amplified by AluIFtaq and AluIRtaq (SEQ ID NOs:22 and 23, respectively) and SEQ ID NO:28 can be used to detect the 8,479 bp AluI control fragment amplicon, as amplified by LargeFtaq and LargeRtaq (SEQ ID NOs: 24 and 25, respectively).

TABLE 4

TaqMan® Probes

| Probe Name | SEQ ID NO: | Probe Sequence |
|---|---|---|
| CGG flanking | 26 | 5'-6-FAM-CTCTGAGCGGGCG-3' |
| AluI control | 27 | 5'-VIC-AGGAAGCTAAGCAGTTG-3' |
| Large control | 28 | 5'-NED-ACTGTACACAACATCG-3' |

Amplified fragments may be detected using standard gel electrophoresis methods. For example, in preferred embodiments, amplified fractions are separated on an agarose gel and stained with ethidium bromide by methods known in the art to detect amplified fragments.

Sizing by Direct PCR Amplification and Electrophoresis

In certain embodiments, direct methods are used to measure the size of tandem repeat regions. In some embodiments, such direct methods are used as a screen prior to the use of the indirect methods disclosed herein. In preferred embodiments, the direct method includes amplification, preferably by PCR. In this method, the entire tandem repeat region is amplified. The resulting amplicons are sized using electrophoresis, preferably capillary electrophoresis.

In one example, forward primer FX-5F (SEQ ID NO:29; 5'GCT CAG CTC CGT TTC GGT TTC ACT TCC GGT 3') is used in an amplification reaction with reverse primer FX-3F (SEQ ID NO:30; 5'-AGC CCC GCA CTT CCA CCA CCA GCT CCT CCA-3') to amplify the tandem repeat region of the FMR1 gene. Preferably, one of the primers of this primer pair is labeled, preferably the label is a fluorescent label. Amplification product may be detected and sized by electrophoresis, preferably capillary electrophoresis. Alternatively, amplification products can be detected and sized using Southern blot.

Correlation of Fragment Size to Normal or Carrier/Affected Status

The fraction in which the marker sequence upstream or downstream of the tandem repeat region is detected corresponds to the size of the fragment containing the tandem repeat. This correlation enables an estimation of the number of tandem repeats and thus, whether an individual is normal or carries an expansion in the tandem repeat region.

In some embodiments, individuals that are afflicted with a disease associated with a mutation in the tandem repeat region of a gene can be distinguished from those that are normal. A nucleic acid sample from the individual is fragmented to produce nucleic acid fragments in which the tandem repeat segment of the gene is associated with a marker sequence in a fragment. The fragments are separated into fractions according to size under conditions in which the fragment(s) containing the tandem repeat segment will be located in the fractions according to the number of repeats in the tandem repeat segment, and identifying those fraction(s) containing the segment by detecting the marker sequence. The fractions are chosen so that one fraction corresponds to tandem repeat regions having a normal number of repeats (i.e., a normal allele) and another fraction that corresponds an abnormal number of repeats (i.e., a mutated allele). If only the former fraction is positive, the individual is normal; if the latter fraction is positive, the individual is affected with the disease. A positive result in both fraction indicates a heterozygote.

In other embodiments, individuals that are normal can be distinguished from those that are carriers of a disease associated with a mutation in the tandem repeat region of a gene, or those that are afflicted with the disease. A nucleic acid sample from the individual is fragmented to produce nucleic acid fragments in which the tandem repeat segment of the gene is associated with a marker sequence in a fragment. The fragments are separated into fractions according to size under conditions in which the fragment(s) containing the tandem repeat segment will be located in the fractions according to the number of repeats in the tandem repeat segment, and identifying those fraction(s) containing the segment by detecting the marker sequence. The fractions are chosen so that a first fraction corresponds to tandem repeat regions having a normal number of repeats (i.e., a normal allele), a second fraction corresponds to tandem repeat regions having a number of repeats in a premutation (i.e., a premutation allele), and a third fraction that corresponds to tandem repeat regions having a number of repeats in a full mutation (i.e., a full mutation allele). Generally, if only the first fraction is positive, the individual is normal; if the second fraction is positive, the individual is a carrier of the disease, and if the third fraction is positive, the individual is affected with the disease. A positive result in more than one fraction indicates a heterozygote. A heterozygote may be a carrier or an affected individual depending on the gene involved.

In some embodiments, individuals afflicted with fragile X syndrome (those having a full mutation) can be distinguished from individuals that are carriers (those having a premutation) or those that are normal. A nucleic acid sample from the individual is fragmented to produce nucleic acid fragments in which the tandem repeat segment of the FMR1 gene is associated with a marker sequence in a fragment. The fragments are separated into fractions according to size under conditions in which the fragment(s) containing the tandem repeat segment will be located in the fractions according to the number of repeats in the tandem repeat segment, and identifying those fraction(s) containing the segment by detecting the marker sequence. The fractions are chosen so that a first fraction corresponds to tandem repeat regions having a normal number of repeats (i.e., a normal allele), a second fraction corresponds to tandem repeat regions having a number of repeats in a premutation (i.e., a premutation allele), and a third fraction that corresponds to tandem repeat regions having a number of repeats in a full mutation (i.e., a full mutation allele). In preferred embodiments, the fractions are chosen so that the first fraction corresponds to tandem repeat regions having less than 55 repeats, the second corresponds to tandem repeat regions having 55-200 repeats, and the third corresponds to tandem repeat regions having greater than 200 repeats. Therefore, if the first fraction is positive (i.e., the marker sequence was detected in this fraction), it indicates that the tandem repeat region contains less than 55 repeats (i.e., a normal allele), if the second fraction is positive, it indicates that the tandem repeat region contains 55-200 repeats (i.e., a premutation allele), and if the third fraction is positive, it indicates that the tandem repeat contains greater than 200 repeats (i.e., a full mutation). If only the first fraction is positive, the individual is normal; if the second fraction is positive, the individual is a carrier; if the third fraction is positive, the individual is afflicted with fragile X. A positive result more than one fraction indicates a heterozygote.

In certain embodiments of an assay to distinguish individuals having a normal tandem repeat region of the FMR1 gene from those having a premutation or full mutation, two fractions of AluI fragmented genomic DNA are separated by capillary electrophoresis and collected by automatic fraction collector, one between 211-400 bp, one between 401 bp-9 kb. AluI fragments having 6-68 repeats will be present in the lower fraction, thus normal alleles and those with small permutations (i.e., 55-68 repeats) will be separated into this fraction. Normal alleles and small premutions can be further distinguished by direct amplification of the tandem repeat region and sizing with electrophoresis. The premutation, encompassing a range of 69-200 repeats, and the full mutation, encompassing 201-2000+repeats will be present in the upper fraction. Therefore, if the lower fraction is positive (i.e., the marker sequence was detected in this fraction), it indicates that there is a CGG tandem repeat region that contains 6-68 repeats; if the upper fraction is positive, it indicates that there is CGG tandem repeat region that contains 68-2000+ repeats. A positive result in both fractions would indicate a heterozygote in which one allele is normal and the other allele contains the premuation or the full mutation.

In other embodiments of the assay to determine size of the tandem repeat region of the FMR1 gene, DNA fragmented with a combination of BlpI an dMlyI is separated into four fractions corresponding to sizes of approximately less than or equal to 603 bp (first/lowest fraction), 604-840 bp (second fraction), 841-1078 bp (third fraction) and 1079 bp-9 kb (fourth/highest fraction). Fragments from samples containing a normal FMR1 gene (i.e., less than 55 tandem repeats) and those containing permutations having 56-62 tandem repeats will separate into the first/lowest fraction. Normal alleles and small premutions can be further distinguished by direct amplification of the tandem repeat region and sizing with electrophoresis. Fragments from FMR1 genes containing small premutations (i.e., 63-140 tandem repeats) will separate into the second fraction, whereas fragments from FMR1 genes containing large permutations (i.e., 141-200 tandem repeats) and full mutations having 201-220 tandem repeats will separate into the third fraction, and whereas large premutations having greater than 220 tandem repeats will separate into the fourth/highest fraction. Large premuations 141-200 repeats can be distinguished from full mutations of 201-220 using, for example, standard Southern blot methods.

In another embodiment, the AluI digested genomic DNA is size fractionated using capillary electrophoresis into a multiplicity of fractions. Automated fraction collection is accomplished using a preset fraction time window of approximately 30 seconds per fraction, beginning at 200 bp and ending at 9 Kb. Approximately 16 fractions are collected. The fraction or fractions that are positive for detection of the marker sequence upstream or downstream of the tandem repeat region correspond to a size range and thus, the number tandem repeats can be estimated.

The following examples serve to illustrate the present invention. These examples are in no way intended to limit the scope of the invention.

Example 1

Restriction Enzyme Digestion

This example describes methods to detect expansion of the tandem repeat region of the FMR1 gene. Genomic DNA test samples and control samples of DNA were restriction endonuclease digested with AluI. 1.0 µg of test or control DNA was used for each digest. Genomic DNA was purified and diluted to a concentration of 50 ng/µL. The reaction mix for the digest was prepared according to the following table.

TABLE 5

AluI reaction mix

| Reagent | (µL/sample) |
| --- | --- |
| 10X NEBuffer 2 | 3.0 |
| AluI (10 U/µL) | 1.0 |
| Sterile H$_2$O | 7.0 |
| Total | 10.0 |

10 µL of the AluI reaction mix was added to each sample of DNA. The samples were mixed by vortexing and spinning in a microfuge and are then incubated overnight at 37° C.

Example 2

Size Separation of Digested DNA

A. Two Fraction Approach

Restriction enzyme digested DNA as described in Example 1 was separated into fractions according to size. 1 kb DNA ladder and the digested test genomic DNA samples were placed into a 96-well plate. The plate was subjected to auto-sampling and automatic fractionation using a Beckman Coulter P/ACE MDQ Series Capillary Electrophoresis System in reversed polarity separation mode. The ladder was first injected into the capillary with 6 kv/60 sec, then run with 200 V/cm to determine the correct sizing cutoff time. Automated fraction collection was accomplished using a preset fractionation time window corresponding to 211-400 bp (lower fraction) and 401 bp-9 kb (upper fraction). The separations are monitored on-column by UV detection. The data were acquired and evaluated by the P/ACE MDQ 32 Karat software package.

The digested samples were fractionated using the same conditions as the 1 kb DNA ladder. The lower fraction (211-396 bp) and the upper fraction (396 bp-9 kb) were collected based on the sizing cutoff times as determined using the 1 kb ladder for each size range. Fractions were collected using the P/ACE MDQ auto-collector and stored in a 96-well plate in 30 µL 0.1×TBE buffer per well.

A. 16 Fraction Approach

Automated fraction collection was accomplished using a preset fractionation time window 30 seconds per fraction, starting roughly form 200 bps and ending at 9 Kbs. The separations were monitored on-column by UV detection. The data were acquired and evaluated by the P/ACE MDQ 32 Karat software package.

1-kb DNA ladder and the digested genomic DNA samples were placed into a 96 well plate. The plate was subjected to autosampling, automatic fractionation on the Beckman Coulter P/ACE MDQ machine with cooling control. The ladder was first electronkinetic injected into the capillary with 6 kv/60 sec, then run with 200 V/cm to determine the correct sizing window (preferably 200 bps-9 Kbs).

The digested samples were fractionated based on the same condition as the 1-kb DNA ladder running condition. A total 16 fractions were collected using P/ACE MDQ's auto collector and stored in a 96-well plate in 5 µL dH$_2$O per well.

Example 3

PCR Amplification and Detection of Fragments with Tandem Repeats

In an assay to detect mutations characterized by an expansion of the tandem repeat region of the FMR1 gene, working PCR master mixes were made as described.

A. PCR Amplification (Non-TaqMan)

A PCR Master Mix for amplifying fragments and for size separation analysis of PCR product was prepared as shown in Table 6.

TABLE 6

Preparation of PCR primer (non-Taqman) master mix for CCG 5' flanking sequence

| Stock Solution | One Reaction (µL) | 500 Reactions (µL) | Final Concentration |
| --- | --- | --- | --- |
| 10X PCR Buffer (with 15 mM MgCl$_2$) | 2.5 | 1250 | 1X (1.5 mM) |
| 5X Q-Solution | 5.00 | 2500 | 1X |
| 25 mM MgCl$_2$ | 0.5 | 250 | 0.5 mM |
| 25 mM dNTPs | 0.2 | 100 | 0.2 mM |
| 100 µM FMR1F4 Primer (SEQ ID NO: 4) | 0.5 | 250 | 2.0 µM |
| 100 µM FMR1R4 Primer (SEQ ID NO: 5) | 0.5 | 250 | 2.0 µM |
| 100 µM AluIF Primer (SEQ ID NO: 10) | 0.1 | 50 | 0.4 µM |
| 100 µM AluIR Primer (SEQ ID NO: 11) | 0.1 | 50 | 0.4 µM |
| 100 µM LargeF Primer (SEQ ID NO: 14) | 0.10 | 50 | 0.4 µM |
| 100 µM LargeR Primer (SEQ ID NO: 15) | 0.10 | 250 | 0.4 µM |
| DMSO | 1.25 | 625 | 5% |
| 1M KCl$_2$ | 1.25 | 625 | 50 mM |
| dH$_2$O | 7.5 | 3750 | |
| Total | 19.6 | 9800 | |

The PCR primer master mix was stored in 1.5 mL aliquots at −20° C. prior to use. When ready for use, PCR reactions were prepared as shown in Table 7.

TABLE 7

Final. PCR amplification mixture for CCG 5' flanking sequence

| Reagent | Per Rxn (µL) | ½ plate (µL) | full plate (µL) |
|---|---|---|---|
| Master Mix | 19.6 | 940.8 | 1881.6 |
| HotStar Taq | 0.4 | 19.2 | 38.4 |
| DNA fraction | 5.0 | — | — |
| Total | 25.0 | 1200 | 2400 |

The final amplification mixtures were sealed tightly in plates with Microseal A film. The plates were vortexed briefly (approximately 5 sec) and spun down for approximately 30 sec in a plate centrifuge at 2,000-6,000 g (1,600 rpm in a Sorvall T6000D centrifuge). The plate was transferred to the ABI 9700 thermal cycler.

The thermal cycler conditions for amplification were as follows:

| | |
|---|---|
| Step 1 | 95° C. for 15 minutes. |
| Step 2 | 95° C. for 60 seconds. |
| Step 3 | 64° C. for 60 seconds. |
| Step 4 | 72° C. for 30 seconds |
| Step 5 | Steps 2-4 repeated, 34 times. |
| Step 6 | 72° C. for 5 minutes. |
| Step 7 | 4° C. indefinitely. |

PCR products were then loaded onto the ABI 3100 genetic analyzer for detection.

B. TaqMan® PCR amplification

A TaqMan® PCR master mix for detecting CCG 5' flanking sequence was prepared as shown in Table 8.

TABLE 8

Preparation of Taqman ® PCR master mix for CCG 5' flanking sequence

| Stock Solution | One Reaction (µL) | 500 Reactions (µL) | Final Concentration |
|---|---|---|---|
| 5X Q-Solution | 10.00 | 5000 | 1X |
| 25 mM MgCl₂ | 1.0 | 500 | 0.5 mM |
| 100 µM FMR1F4 Primer (SEQ ID NO: 4) | 1.0 | 500 | 2.0 µM |
| 100 µM FMR1R4 Primer (SEQ ID NO: 5) | 1.0 | 500 | 2.0 µM |
| 100 µM AluIFtaq Primer (SEQ ID NO: 22) | 0.40 | 200 | 0.8 µM |
| 100 µM AluIRtaq Primer (SEQ ID NO: 23) | 0.40 | 200 | 0.8 µM |
| 100 µM LargeFtaq Primer (SEQ ID NO: 24) | 0.40 | 200 | 0.8 µM |
| 100 µM LargeRtaq Primer (SEQ ID NO: 25) | 0.40 | 200 | 0.8 µM |
| DMSO | 2.50 | 1250 | 5% |
| 1 M KCl₂ | 2.50 | 1250 | 50 mM |
| CGG Flanking Probe (SEQ ID NO: 26) | 0.10 | 100 | 0.2 µM |
| AluI Control Probe (SEQ ID NO: 27) | 0.10 | 100 | 0.2 µM |
| Large Control Probe (SEQ ID NO: 28) | 0.10 | 100 | 0.2 µM |
| dH₂O | 0.10 | 100 | |
| Total | 20 | 10000 | |

The TaqMan® PCR master mix was stored in 1.5 mL aliquots at −20° C. prior to use. When ready for use, TaqMan® PCR reactions were prepared as shown in Table 9.

TABLE 9

TaqMan® PCR Master Mix

| Reagents | 1 reaction (µL) | ¼ plate (µL) | ½ plate (µL) | ¾ plate (µL) | full plate (µL) |
|---|---|---|---|---|---|
| TaqMan 2X Universal Master Mix | 25.0 | 750 | 1600 | 2150 | 2750 |
| Primer/Probe Mix | 20.0 | 600 | 1280 | 1720 | 2200 |
| Total | 45.0 | 1350 | 2880 | 3870 | 4950 |

45 µL of the TaqMan® PCR master mix was added to each well of the 96-well plate containing the fractions of size separated DNA. The wells are sealed tightly with Microseal A film. The plates were vortexed briefly (approximately 5 see) and spun down for approximately 30 sec in a plate centrifuge at 2,000-6,000 g (1,600 rpm in a Sorvall® T6000D centrifuge). The plate was transferred to the ABI 7700 (or 790011T) sequence detector.

The thermocycler conditions for TaqMan® were as follows:

| | |
|---|---|
| Step 1 | 95° C. for 15 minutes. |
| Step 2 | 95° C. for 60 seconds. |
| Step 3 | 64° C. for 60 seconds. |
| Step 4 | 72° C. for 30 seconds |
| Step 5 | Steps 2-4 repeated, 40 times. |
| Step 6 | 72° C. for 5 minutes. |
| Step 7 | 4° C. indefinitely. |

Example 4

Detection of Amplified Fractions by Gel Electrophoresis

Gel electrophoresis was used to identify the size of PCR amplified fragments prepared as described in Example 3A. 6 µL of 6×FEB (Ficoll® EDTA bromophenol blue loading dye) was added to 6 µL PCR products and the resulting mixture was loaded into the gel. 50 by DNA ladder was loaded into the first and last well of the gel. Samples were electrophoresed in 0.8% agarose at 200V for 1.5 hours. Completed gel was photographed with UV photodocumentation apparatus (Alpha Innotech Image Analysis System).

Example 5

Detection of Expansion Mutations of the Tandem Repeat Region of the DM-1 Gene

In an assay to detect mutations characterized by an expansion of the tandem repeat region of the DM-1 gene, genomic DNA test samples are restriction endonuclease digested with AluI. Approximately 1.0 µg of test genomic DNA is used for each digest. The reaction mix for the digest is prepared according to the enzyme supplier's protocol. The samples are mixed and incubated at 37° C. to complete digestion.

The restriction enzyme digested DNA is separated according to size using capillary electrophoresis and two fractions are collected, such that the first fraction (250-360 bp) corresponds to the normal repeat range (e.g., 5-37 repeats) and the second fraction (400 bp-9 kb) corresponds to an expanded repeat mutation (e.g., greater than 50 repeats). 1 kb DNA ladder is first injected into the capillary to determine the correct sizing cutoff time. Automated fraction collection is accomplished using a preset fractionation time window corresponding to a lower fraction and an upper fraction. The separations are monitored on-column by UV detection. The digested samples are then fractionated using the same conditions as the 1 kb DNA ladder. The lower fraction and the upper fraction are collected based on the sizing cutoff times as determined using the 1 kb ladder for each size range.

Each fraction is analyzed using the TaqMan® real time PCR method for the presence of a fragment containing the DM-1 tandem repeat region. In this method, a segment of the 3'-untranslated region of DM-1 gene is amplified using a forward primer (e.g., 5'-CCATTTCTTTCTTTCGGCCA-3'; SEQ ID NO:31) and a reverse primer (e.g., 5'AGGCCTG-CAGTTTGCCC-3'; SEQ ID N©:32). The amplified fragment is detected with a TaqMan® labeled probe, 5'-TGAG-GCCCTGACGTGG-3' (SEQ ID NO:33).

The presence of the amplified segment in only the lower fraction is indicative of an individual homozygous for the normal DM-1 allele. The presence of the amplified segment in only the upper fraction is indicative of an individual homozygous for a mutant allele(s). The presence of the amplified segment in both fractions is indicative of a heterozygote.

Example 6

Detection of Expansion Mutations of the Tandem Repeat Region of the FRDA Gene

In an assay to detect mutations characterized by an expansion of the tandem repeat region of the FRDA gene, genomic DNA test samples are restriction endonuclease digested with AluI and RsaI. Approximately 1.0 μg of test genomic DNA is used for each digest. The reaction mix for the digest is prepared according to the enzyme supplier's protocol. The samples are mixed and incubated at 37° C. to complete digestion.

The restriction enzyme digested DNA is separated according to size using capillary electrophoresis and two fractions are collected, such that the first fraction (300-405 bp) corresponds to the normal repeat range (e.g., 7-34 repeats) and the second fraction (600 bp-9 kb) corresponds to an expanded repeat mutation (e.g., greater than 100 repeats). 1 kb DNA ladder is first injected into the capillary to determine the correct sizing cutoff time. Automated fraction collection is accomplished using a preset fractionation time window corresponding to a lower fraction and an upper fraction. The separations are monitored on-column by UV detection. The digested samples are then fractionated using the same conditions as the 1 kb DNA ladder. The lower fraction and the upper fraction are collected based on the sizing cutoff times as determined using the 1 kb ladder for each size range.

Each fraction is analyzed using the TagMan® real time PCR method for the presence of a fragment containing the FRDA tandem repeat region. In this method, a segment of the first intronic region of the FRDA gene is amplified using a forward primer 5'-AGGCCTAGGAAGGTGGATCAC-3'; SEQ ID NO:34) and a reverse primer (e.g., 5'-ACCATGTTG-GCCAGGTTAGTCT-3'; SEQ ID NO:35). The amplified fragment is detected with a TagMan® labeled probe, 5'-TGAGGTCCGGAGTTC-3' (SEQ ID NO:36).

The presence of the amplified segment in only the lower fraction is indicative of an individual homozygous for the normal FRDA allele. The presence of the amplified segment in only the upper fraction is indicative of an individual homozygous for a mutant allele(s). The presence of the amplified segment in both fractions is indicative of a heterozygote.

Example 7

Detection of Expansion Mutations of the Tandem Repeat Region of the FMR1 Gene

In this example, expansion mutations of the tandem repeat region of the FMR1 gene were detected by fragmentation with AluI, size fractionation, followed by a second restriction enzyme digestion with BstNI. Thus, genomic DNA test samples were restriction endonuclease digested with AluI as described above in Example 1. The digested DNA was then fractionated into four fractions using capillary electrophoresis. Fraction 1 contains nucleic acids with 0-60 CCG tandem repeats, fraction 2 contains 60-200 CCG tandem repeats, fraction 3 contains 200-2000 CCG tandem repeats and fraction 4 contains 2000+CCG tandem repeats. Following fractionation, an aliquot of each of the four fractions was digested with a second restriction endonuclease, BstNI, that cleaved the marker from the CCG tandem repeat region. Following the second nucleic acid fractionation, each of the four fractions were subjected to PCR as described in Example 3B (i.e., TaqMan® PCR Amplification).

A. Second Restriction Enzyme Digestion of Samples from Affected Individuals

Affected samples were tested with and without a second restriction enzyme digestion in which the marker sequence was cleaved from the tandem repeat region. Samples having the second digestion had much stronger signals (i.e., higher relative fluorescence unit (RFU) signals) as compared to samples that did not undergo a second enzyme digestion. Each sample was run in duplicate; data are shown below in table 9. These data suggest that there is increased amplification of the marker sequence when the marker sequence is cleaved from the tandem repeat region.

TABLE 10

Relative Fluorescence Unit (RFU) Signals of Affected Samples With ("with 2°") and Without a Second Restriction Enzyme Digestion ("without 2°").

| Sample No. | Fraction 1 | Fraction 2 | Fraction 3 | Fraction 4 |
|---|---|---|---|---|
| 15251 without 2° | 75 | 0 | 445 | 0 |
| Duplicate | 0 | 0 | 0 | 0 |
| 15251 with 2° | 1752 | 781 | 787 | 0 |
|  | 2566 | 931 | 695 | 0 |
| 15050 without 2° | 980 | 0 | 210 | 0 |
|  | 259 | 0 | 318 | 0 |
| 15050 with 2° | 3571 | 0 | 873 | 0 |
|  | 2270 | 586 | 1042 | 0 |
| 14792 without 2° | 575 | 0 | 328 | 0 |
|  | 662 | 280 | 246 | 0 |
| 14792 with 2° | 1223 | 243 | 658 | 0 |
|  | 1308 | 450 | 967 | 0 |

B. Second Restriction Enzyme Digestion of Samples from Normal Individuals

Normal samples were tested with and without a second restriction enzyme digestion in which the marker sequence was cleaved from the tandem repeat region. Samples having less starting material that underwent the second digestion, had comparable or higher signals (i.e., higher relative fluorescence unit (RFU) signals) as compared to samples having more starting material that did not undergo a second enzyme digestion. Data are shown below in table 10. These data suggest that there is increased amplification of the marker sequence when the marker sequence is cleaved from the tandem repeat region.

TABLE 11

Relative Fluorescence Unit (RFU) Signals of Normal Samples With ("with 2°") and Without a Second Restriction Enzyme Digestion ("without 2°").

| Sample No. | Fraction 1 | Fraction 2 | Fraction 3 | Fraction 4 |
|---|---|---|---|---|
| 14028 without 2° | 3044 | 0 | 0 | 0 |
| 14028 with 2° | 4356 | 0 | 0 | 0 |
| 13616 without 2° | 2701 | 0 | 0 | 0 |
| 13616 with 2° | 2396 | 0 | 0 | 0 |
| 13488 without 2° | 1399 | 0 | 0 | 0 |
| 13488 with 2° | 2258 | 0 | 0 | 0 |
| 13524 without 2° | 1051 | 0 | 0 | 0 |
| 13524 with 2° | 1074 | 0 | 0 | 0 |

Example 8

Detection of Expansion Mutations of the Tandem Repeat Region of the FMR1 Gene

In this example, expansion mutations of the tandem repeat region of the FMR1 gene are detected by fragmentation with BlpI and MlyI, size fractionation, followed by a second restriction enzyme digestion with BmtI.

Genomic DNA test samples are restriction endonuclease digested with BlpI and MlyI using approximately 1.5 µg of test or control DNA (purified and diluted to a concentration of 50 ng/µL) for each digest. The reaction mix for the digest is prepared according to the following table.

TABLE 12

| BlpI/MlyI reaction mix | |
|---|---|
| Reagent | (µL/sample) |
| Genomic DNA 50 ng/µL | 30 µL |
| 10X NEBuffer 4 (New England BioLabs) | 3.5 |
| BlpI (10 U/µL) | 0.75 |
| MlyI (10 U/µL) | 0.75 |
| Total | 35.0 |

The samples are mixed by vortexing and spinning in a microfuge and are then incubated at 37° C. for 16 hours and stored at 4° C. The digested DNA is then fractionated into four fractions using capillary electrophoresis using P/ACE™ MDQ Capillary Electrophoresis System. Fraction 1 (less than 603 bp) contains nucleic acids with 6-62 CCG tandem repeats, fraction 2 (603-840 bp) contains 63-140 CCG tandem repeats, fraction 3 (841-1078 bp) contains 141-220 CCG tandem repeats and fraction 4 (1079 bp-9 kb) contains 221-2000+CCG tandem repeats. Following fractionation, an aliquot of each of the four fractions is digested with the restriction endonuclease, BmtI, which cleaves the marker from the CCG tandem repeat region. The BmtI reaction mix is prepared according to the following table.

TABLE 13

| BmtI reaction mix | |
|---|---|
| Reagent | (µL/sample) |
| Fractionated genomic DNA | 30 µL |
| 10X NEBuffer 2 (New England BioLabs) | 3.0 |
| BmtI (10 U/µL) | 0.75 |
| Total | 33.75.0 |

The digestion reaction mixes are incubated at 37° C. for 16 hours and stored at 4° C.

Following the second nucleic acid digestion, each of the four fractions are subjected to PCR using the following primers:

TABLE 14

Primers for PCR amplification of BlpI/MlyI fragments

| Primer Name | SEQ ID NO: | Primer Sequence |
|---|---|---|
| FXCEF2 | 6 | 5'-/6-FAM/GATGGAGGAGCTGGTGGTGG-3' |
| FXCER2 | 7 | 5'-GGAAGGGCGAAGATGGGG-3' |
| BlpIF | 12 | 5'-/HEX/AGTGTTTAGAAGGAAAAGGCTGAGC-3' |
| BlpIR | 13 | 5'-GCCCAAAGTTTCATAGGTAGCAAA-3' |
| FIIctrlIF | 16 | 5'-/HEX/CTGAATTTGTTTGGTTTGATGATGC-3' |
| FIIctrlIR | 17 | 5'-CCTGTGTTATCTGTGCCCATTTTAA-3' |
| FIIIctrl3F | 18 | 5'-/6-FAM/ATCTGGGTCTGAATAATGTGAGGAG-3' |
| FIIIctrl3R | 19 | 5'-CCTAACTTTCATTCTTGTCACCCTT-3' |
| LgctrlF | 20 | 5'-/6-FAM/AGGTTTGAGTGTATCGCCTGATAGA-3' |
| LgctrlR | 21 | 5'-TGAGTTTCATGTTTGCTCTTGCTC-3' |

A PCR master mix for amplifying fragments for size analysis is prepared according to Table 15.

TABLE 15

| PCR Master Mix | | |
|---|---|---|
| Reagent | Vol. for 1 reaction (µL) | Final Conc in PCR Reaction |
| Qiagen 10X Buffer | 2.5 | 1X |
| Qiagen 25 mM MgCl$_2$* | 0.75 | 2.25 mM |
| DMSO | 1.25 | 5% (v/v) |
| 1 M KCl** | 1.25 | 105 mM |
| 25 mM dNTP | 0.2 | 0.2 mM |
| 100 µM FXCEF2 | 0.25 | 1 µM |
| 100 µM FXCER2 | 0.25 | 1 µM |
| 100 µM BlpIF | 0.015 | 0.06 µM |
| 100 µM BlpIR | 0.015 | 0.06 µM |
| 100 µM lgctrlF | 0.06 | 0.24 µM |
| 100 µM lgctrlR | 0.06 | 0.24 µM |
| 100 µM FIIctrl1F | 0.015 | 0.06 µM |

TABLE 15-continued

PCR Master Mix

| Reagent | Vol. for 1 reaction (μL) | Final Conc in PCR Reaction |
|---|---|---|
| 100 μM FIIctrl1R | 0.015 | 0.06 μM |
| 100 μM FIIIctrl3F | 0.02 | 0.08 μM |
| 100 μM FIIIctrl3R | 0.02 | 0.08 μM |
| Water | 12.83 | |
| Total | 19.5 | |

*, **2.5 μL 10X PCR buffer contains 15 mM MgCl$_2$, 50 mM KCl.
Total reaction MgCl$_2$ is 2.25 mM, KCl is 105 mM.

A final PCR amplification mixture is made by adding 0.5 μL HotStarTaq® (Qiagen) is added to each individual PCR reaction followed by 5 μL digested fractionated DNA. The final amplification mixtures are scaled tightly in plates with Microseal® A film. The plates are vortexed briefly (approximately 5 sec) and spun down for approximately 30 sec in a plate centrifuge at 2,000-6,000 g (1,600 rpm in a Sorvall® T6000D centrifuge). The plate is transferred to the ABI 9700 thermal cycler.

The thermal cycler conditions for amplification are as follows:

| Step 1 | 95° C. for 15 minutes. |
|---|---|
| Step 2 | 95° C. for 30 seconds |
| Step 3 | 55° C. for 30 seconds. |
| Step 4 | 72° C. for 60 seconds |
| Step 5 | Steps 2-4 repeated, 33 times. |
| Step 6 | 72° C. for 10 minutes. |
| Step 7 | 4° C. indefinitely. |

2 μL PCR product is combined with 10.5 μL Hi-Di formamide (Applied Biosystems) with ROX 350 size standard (Applied Biosystems), heated at 95° C. for 5 minutes followed by 5 minutes on ice. Samples are then loaded onto the ABI 3100 genetic analyzer for detection.

Example 9

Detection of Expansion Mutations of the Tandem Repeat Region of the FMR1 Gene

In this example, expansion mutations of the tandem repeat region of the FMR1 gene are detected by fragmentation with SphI and BmtI, size fractionation, followed by a second restriction enzyme digestion with BstNI. Thus, genomic DNA test samples are restriction endonuclease digested with SphI and BmtI using approximately 1.5 μg of test or control DNA (purified and diluted to a concentration of 50 ng/μL) for each digest. The reaction mix for the digest is prepared according to the following table.

TABLE 16

SphI/BmtI reaction mix

| Reagent | (μL/sample) |
|---|---|
| Genomic DNA (50 ng/μL) | 30 |
| 10X NEBuffer 2 (New England BioLabs) | 3.5 |
| SphI (10 U/μL) | 0.75 |
| BmtI (10 U/μL) | 0.75 |
| Total | 35.0 |

The samples are mixed by vortexing and spinning in a microfuge and are then incubated overnight at 37° C. The digested DNA is then fractionated into four fractions using capillary electrophoresis. Fraction 1 contains nucleic acids with 6-62 tandem repeats, fraction 2 contains 63-163 tandem repeats, fraction 3 contains 164-196 tandem repeats and fraction 4 contains greater than tandem repeats. Following fractionation, an aliquot of each of the four fractions is digested with a second restriction endonuclease, BmtI, that cleaved the marker from the CCG tandem repeat region. Following the second nucleic acid fractionation, each of the four fractions are subjected to PCR using the following primers:

TABLE 17

Primers for PCR amplification of SphI/BmtI fragments

| Primer Name | SEQ ID NO: | Primer Sequence |
|---|---|---|
| FXCEF3 | 8 | 5'-CGTGACGTGGTTTCAGTGTTTACA-3' |
| FXCER3 | 9 | 5'-GGAAGTGAAACCGAAACGGAG-3' |

PCR is conducted using the following conditions:

| Step 1 | 95° C. for 15 minutes. |
|---|---|
| Step 2 | 95° C. for 30 seconds |
| Step 3 | 55° C. for 30 seconds. |
| Step 4 | 72° C. for 60 seconds |
| Step 5 | Steps 2-4 repeated, 33 times. |
| Step 6 | 72° C. for 10 minutes. |
| Step 7 | 4° C. indefinitely. |

PCR products are then loaded onto the ABI 3100 genetic analyzer for detection.

Example 10

Identification of a Control Fragment for Use in the FMR1 Assay

An AluI fragment from a region of the genome distinct from FMR1, that was larger than 6000 bases, containing trinucleotide repeats, and having a high GC content and/or CpG islands was identified for use as a control fragment in the FMR1 assay. This fragment was identified as follows. All AluI sites in the human genome were identified using the EMBOSS Restrict program (Rice et al., "EMBOSS: The European Molecular Biology Open Software Suite." *Trends in Genetics* 16(6):276-7 (2000)), resulting in a predicted 11.5 million fragments produced by a digestion with AluI. From these fragments, 20 fragments having a length longer than 6000 bases were identified using the TACG program (Mangalam, H J. "tacg—a grep for DNA." *BMC Bioinformatics* 3:8 (2002)). The sequences of these 20 fragments were obtained using EMBOSS ExtractSeq. Of these 20 fragments, one fragment corresponding to a region of the USP41 gene on chromosome 22 (i.e., chromosome 22:19033185-19041663) was found to have a large trinucleotide repeat region. The GC content was analyzed using EMBOSS geecee and the CpG island analysis was performed using EMBOSS cpgseek and newcpgreport.

Example 11

Determination of the Size of the Tandem Repeat Region of FMR1 Using PCR

To determine the size of the tandem repeat region of the FMR1 region, the region is amplified by the polymerase chain reaction in the presence of a fluorescently-labeled primer (e.g., 6-FAM) and the sizes of the resulting labeled amplicons are determined by capillary electrophoresis. A second trinucleotide repeat (CAG in the X-linked androgen receptor gene) is co-amplified using a primer pair in which one of the primers is fluorescently-labeled and co-analyzed to provide an internal amplification control.

Thus, the tandem repeat region of the FMR1 gene is amplified using FX-5F (SEQ ID NO:29) as the forward primer and FX-3F (SEQ ID NO:30) as the reverse primer, and trinucleotide repeat of the X-linked androgen receptor gene using AR-5F (SEQ ID NO:37) as the forward primer and AR-R2 (SEQ ID NO:38) as the reverse primer, as set forth in the table below.

TABLE 18

Primers for PCR amplification

| Primer Name | SEQ ID NO: | Primer Sequence |
|---|---|---|
| FX-5F | 29 | 5'-(6-FAM) GCT CAG CTC CGT TTC GGT TTC ACT TCC GGT 3' |
| FX-3F | 30 | 5'-AGC CCC GCA CTT CCA CCA CCA GCT CCT CCA-3' |
| AR-5F | 37 | 5'-(HEX) ACC AGG TAG CCT GTG GGG CCT CTA CGA TGG GC-3' |
| AR-R2 | 38 | 5'-GCT TTC CAG AAT CTG TTC CAG AGC GTG CGC GA-3' |

A PCR master mix for amplifying fragments for size analysis is prepared according to Table 19.

TABLE 19

PCR Master Mix

| Reagent | Vol. for 1 reaction (µL) | Vol. for 1000 reactions (µL) |
|---|---|---|
| 10X Buffer (Qiagen) | 1.0 | 1000 |
| Qiagen 25 mM MgCl$_2$ (Qiagen) | 0.2 | 200 |
| 25 mM dNTP | 0.08 | 80 |
| 100 µM FX-5F primer | 0.04 | 40 |
| 100 µM FX-3F primer | 0.04 | 40 |
| 100 µM AR-5F primer | 0.04 | 40 |
| 100 µM AR-R2 primer | 0.04 | 40 |
| DMSO | 0.2 | 200 |
| 5X Q (Betaine) solution | 5.0 | 5,000 |
| Water | 1.16 | 1,160 |
| Total | 10.0 | |

The PCR master mix is aliquoted into 1,100 µL aliquots to which 5.5 µL of Taq polymerase (5 U/µL) from Qiagen and 22 µL of Pfu DNA polymerase (2.5 U/µL) from Stratagene are added to make the polymerase/master mix solution.

Genomic DNA is diluted to 20 ng/µL in TE buffer. Samples are heated to 93-97° C. for 4-6 minutes and cooled on ice. 10 µL of polymerase/master mix solution is added to 2 µL (40 ng) diluted genomic DNA.

The samples are transferred to the ABI 9700 thermal cycler once the thermal cycler has reached 85° C.+/−2° C. The PCR conditions for amplification are as follows:

| Step 1 | 95° C. for 6 minutes |
| Step 2 | 95° C. for 1 minute |
| Step 3 | 60° C. for 2 minutes |
| Step 4 | 75° C. for 5 minutes |
| Step 5 | Steps 2-4 repeated, 31 times |
| Step 6 | 75° C. for 13 minutes |
| Step 7 | 4° C. indefinitely. |

PCR products are then loaded onto the ABI 3100 genetic analyzer for detection.

Unless otherwise defined, all technical and scientific terms used herein have the same meaning as commonly understood by one of ordinary skill in the art to which this invention belongs. All nucleotide sequences provided herein are presented in the 5' to 3' direction.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A method of detecting a mutation in a tandem repeat segment of a gene in a human genomic nucleic acid sample comprising a nucleic acid segment and a marker sequence, wherein said mutation is characterized by a change in the number of repeats compared to the number of repeats in the wild type allele, said method comprising
   a) fragmenting the nucleic acid sample into fragments, wherein said tandem repeat segment is associated with a marker sequence in at least one of said fragments;
   b) separating said fragments from a) into liquid fractions according to size under conditions in which the fragment(s) containing the tandem repeat segment will be located in said liquid fractions according to the number of repeats in the tandem repeat segment;
   c) subjecting said fragments from said one or more liquid fractions of b) to a second fragmentation such that all or a portion of the segment is cleaved from said marker sequence;
   d) identifying the segment by amplifying and detecting the marker sequence within said one or more liquid fractions from c), wherein the number of repeats in the tandem repeat segment is determined by the liquid fraction in which it is identified in b), and
   e) comparing the number of repeats in the tandem repeat segment determined in d) to the number in the corresponding wild type allele, wherein a number of repeats differing from the number in the wild type allele is indicative of a mutation.

2. A method according to claim 1, wherein said second fragmentation in c) is performed using a restriction endonuclease.

3. A method according to claim 2, wherein said restriction endonuclease used in c) is selected from the group consisting of BsaWI, HphI, BbvI, BstNI, Hpy1881, SmlI, and BmtI.

4. A method according to claim 1, wherein said amplification in d) is accomplished with polymerase chain reaction (PCR).

5. A method according to claim 4, wherein said PCR includes a labeled primer.

6. The method of claim 1, wherein said detecting in d) is accomplished using the Taqman PCR detection system.

7. A method according to claim 1, wherein said tandem repeats are trinucleotide tandem repeats.

8. A method of distinguishing between normal individuals, those that are carriers of fragile X syndrome, and those that are afflicted with fragile X syndrome, said method comprising,
   a) fragmenting the nucleic acid in the sample from the individual into fragments, wherein said tandem repeat segment of the FMR1 gene is associated with a marker sequence in at least one of said fragments,
   b) separating said fragments from a) into liquid fractions according to size under conditions in which the fragment(s) containing the tandem repeat segment having a normal number of repeats will be located in a first liquid fraction; fragments containing a tandem repeat segment having a premutation will be located in a second liquid fraction; and fragments having a tandem repeat region having a full mutation will be located in a third liquid fraction,
   c) subjecting said fragments from each of said liquid fractions in b) to a second fragmentation such that all or a portion of the segment is cleaved from said marker sequence;
   d) identifying the segment by amplifying and detecting the marker sequence within said liquid fractions from c), wherein the number of repeats in the tandem repeat segment is determined by the liquid fraction in which it is identified in b), and wherein
      1) a positive result in only the first liquid fraction indicates the individual is normal;
      2) a positive result in the second liquid fraction indicates the individual is a carrier; and 3) a positive result in the third liquid fraction indicates the individual is afflicted with fragile X syndrome.

9. A method according to claim 8, wherein said second fragmentation in c) is performed using a restriction endonuclease.

10. A method according to claim 9, wherein said restriction endonuclease used in c) is selected from the group consisting of BsaWI, HphI, BbvI, BstNI, Hpy1881, SmlI, and BmtI.

11. A method according to claim 8, wherein said amplification in d) is accomplished with polymerase chain reaction (PCR).

12. A method according to claim 11 wherein said PCR includes a labeled primer.

13. The method of claim 8, wherein said detecting in d) is accomplished using the Taqman PCR detection system.

* * * * *

SEQUENCE LISTING

<160> NUMBER OF SEQ ID NOS: 39

<210> SEQ ID NO 1
<211> LENGTH: 253
<212> TYPE: DNA
<213> ORGANISM: Homo sapiens

```
<400> SEQUENCE: 1
ctccgtttcg gtttcacttc cggtggaggg ccgcctctga gcgggcggcg ggccgacggc     60
gagcgcgggc ggcggcggtg acggaggcgc cgctgccagg gggcgtgcgg cagcgcggcg    120
gcggcggcgg cggcggcggc ggcggaggcg gcggcggcg cggcggcggc ggcggctggg    180
cctcgagcgc ccgcagccca cctctcgggg gcgggctccc ggcgctagca gggctgaaga    240
gaagatggag gag                                                       253

<210> SEQ ID NO 2
<211> LENGTH: 310
<212> TYPE: DNA
<213> ORGANISM: Homo sapiens

<400> SEQUENCE: 2
ctccagtcct gtgatccggg cccgccccct agcggccggg gagggagggg ccgggtccgc     60
ggccggcgaa cggggctcga agggtccttg tagccgggaa tgctgctgct gctgctgctg    120
ctgctgctgc tgctgctgct gctgctgctg ctgctgctgc tgggggatc acagaccatt    180 tctttctttc ggccaggctg aggccctgac gtggatgggc aaactgcagg cctgggaagg    240
cagcaagccg ggccgtccgt gttccatcct ccacgcaccc ccacctatcg ttggttcgca    300
aagtgcaaag                                                           310

<210> SEQ ID NO 3
<211> LENGTH: 168
<212> TYPE: DNA
<213> ORGANISM: Homo sapiens

<400> SEQUENCE: 3
aggcctagga aggtggatca cctgaggtcc ggagttcaag actaacctgg ccaacatggt     60
gaaacccagt atctactaaa aatacaaaa aaaaaaaaa aagaagaaga agaagaagaa    120
aataaagaaa agttagccgg gcgtggtgtc gcgcgcctgt aatcccag                168

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtggagggc cgcctctg                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
agcggcgcct ccgtcacc                                                   18

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
       primer

<400> SEQUENCE: 6
gatggaggag ctggtggtgg                                              20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaagggcga agatgggg                                                18

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgtgacgtgg tttcagtgtt taca                                         24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaagtgaaa ccgaaacgga g                                            21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctccaatgcc tcctgcgtcc                                              20

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggggtaggg agtgtctgag agtct                                        25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 12
agtgtttaga aggaaaaggc tgagc                                        25

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcccaaagtt tcataggtag caaa                                         24

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caccctacaa gccgtcgcta aca                                          23

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgtgccttgt cggtatcatt agcaa                                        25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgaatttgt ttggtttgat gatgc                                        25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cctgtgttat ctgtgcccat tttaa                                        25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
```

```
atctgggtct gaataatgtg aggag                                          25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cctaactttc attcttgtca ccctt                                          25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aggtttgagt gtatcgcctg ataga                                          25

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgagtttcat gtttgctctt gctc                                           24

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcctcctgcg tccttgtaga                                                20

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgagagtctt gtttcagcag tgttaa                                         26

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caagccgtcg ctaacaagga                                                20
```

```
<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatgtcttgt atggtgccct cat                                              23

<210> SEQ ID NO 26
<211> LENGTH: 13
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ctctgagcgg gcg                                                         13

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
aggaagctaa gcagttg                                                     17

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
actgtacaca acatcg                                                      16

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctcagctcc gtttcggttt cacttccggt                                       30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agccccgcac ttccaccacc agctcctcca                                       30

<210> SEQ ID NO 31
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccatttcttt ctttcggcca                                              20

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aggcctgcag tttgccc                                                 17

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
tgaggccctg acgtgg                                                  16

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aggcctagga aggtggatca c                                            21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
accatgttgg ccaggttagt ct                                           22

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
tgaggtccgg agttc                                                   15

<210> SEQ ID NO 37
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
accaggtagc ctgtggggcc tctacgatgg gc                                          32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gctttccaga atctgttcca gagcgtgcgc ga                                          32

<210> SEQ ID NO 39
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccccgccccg cg                                                                12
```